US008232411B2

(12) United States Patent (10) Patent No.: US 8,232,411 B2
Lukin et al. (45) Date of Patent: Jul. 31, 2012

(54) METHODS FOR MAKING CENTRAL NERVOUS SYSTEM AGENTS THAT ARE TRPV1 ANTAGONISTS

(75) Inventors: Kirill A. Lukin, Vernon Hills, IL (US); Brian J. Kotecki, Oak Creek, WI (US); Su Yu, Lake Bluff, IL (US); Lei Wang, Acton, MA (US); Anthony R. Haight, Wadsworth, IL (US)

(73) Assignee: Abbott Laboratories, Abbott Park, IL (US)

( * ) Notice: Subject to any disclaimer, the term of this patent is extended or adjusted under 35 U.S.C. 154(b) by 177 days.

(21) Appl. No.: 12/407,857

(22) Filed: Mar. 20, 2009

(65) Prior Publication Data

US 2010/0016611 A1 Jan. 21, 2010

Related U.S. Application Data

(60) Provisional application No. 61/038,212, filed on Mar. 20, 2008.

(51) Int. Cl.
*C07D 231/56* (2006.01)
*C07C 211/00* (2006.01)
*C07C 237/00* (2006.01)

(52) U.S. Cl. ...................... 548/361.1; 564/163; 564/336

(58) Field of Classification Search ........................ None
See application file for complete search history.

(56) References Cited

U.S. PATENT DOCUMENTS

| | | | |
|---|---|---|---|
| 3,647,819 A | 3/1972 | Kirchner | |
| 3,711,610 A | 1/1973 | Kirchner | |
| 3,814,711 A | 6/1974 | Eloy et al. | |
| 4,958,026 A | 9/1990 | Schoellkopf et al. | |
| 5,362,878 A | 11/1994 | Chang et al. | |
| 5,444,038 A | 8/1995 | James et al. | |
| 5,646,140 A | 7/1997 | Sugg et al. | |
| 5,656,634 A | 8/1997 | Chang et al. | |
| 5,760,246 A | 6/1998 | Biller et al. | |
| 6,001,860 A | 12/1999 | Hamanaka | |
| 6,291,476 B1 | 9/2001 | Kordik et al. | |
| 6,472,414 B1 | 10/2002 | Biller et al. | |
| 6,511,998 B2 | 1/2003 | Kordik et al. | |
| 6,555,539 B2 | 4/2003 | Reich et al. | |
| 6,858,577 B1 | 2/2005 | Zhang et al. | |
| 6,933,311 B2 | 8/2005 | Lee et al. | |
| 7,015,233 B2 | 3/2006 | Gomtsyan et al. | |
| 2004/0157849 A1 | 8/2004 | Lee et al. | |
| 2005/0043351 A1 | 2/2005 | Gomtsyan et al. | |
| 2005/0119304 A1 | 6/2005 | Yura et al. | |

FOREIGN PATENT DOCUMENTS

| | | |
|---|---|---|
| EP | 418071 A2 | 3/1991 |
| EP | 587180 A2 | 3/1994 |
| EP | 609960 A1 | 8/1994 |
| EP | 1256574 A1 | 11/2002 |
| EP | 1403255 A1 | 3/2004 |
| FR | 1344579 A | 11/1963 |
| GB | 2020280 A | 11/1979 |
| WO | WO-9113874 A1 | 9/1991 |
| WO | WO-9726240 A1 | 7/1997 |
| WO | WO-9850347 A1 | 11/1998 |
| WO | WO-0050387 A1 | 8/2000 |
| WO | WO-0208221 A2 | 1/2002 |
| WO | WO-03014064 A1 | 2/2003 |
| WO | WO-03022809 A2 | 3/2003 |
| WO | WO-03055484 A1 | 7/2003 |
| WO | WO-03055848 A2 | 7/2003 |
| WO | WO-03070247 A1 | 8/2003 |
| WO | WO-03080578 A1 | 10/2003 |
| WO | WO-03097586 A1 | 11/2003 |
| WO | WO-2005028445 A2 | 3/2005 |
| WO | 2007/121339 A2 | 10/2007 |
| WO | WO2007121339 A2 | 10/2007 |
| WO | 2008/024945 A1 | 2/2008 |
| WO | WO2008024945 A1 | 2/2008 |

OTHER PUBLICATIONS

International Search Report for Application No. PCT/US2009/037741, Mailed on Oct. 30, 2009, 2 pages.
"IUPAC Commission on Nomenclature of Organic Chemistry—Rules for the Nomenclature of Organic Chemistry, Section E: Stereochemistry (Recommendations 1974)," Pure Appl Chem, 1976, 13-30, vol. 45.
Abad A, "Regioselective Preparation of Pyridin-2-yl Ureas from 2-Chloropyridines Catalyzed by Pd(0)", Synthesis, 2005, 6, 915-924.
Adams, E.P. et al., "Dialkylaminoalkylquinolines," J.Chem.Soc. 1957, 3066-3071.
Berge, S.M. et al., "Pharmaceutical Salts," J Pharmaceutical Sciences, 1977, 1-19, vol. 66.
Cannon, J.G. et al., "Synthesis of N-alkyl derivatives of 4-(2'-aminothyl)indole," J.Heterocyclic Chemistry, 1982, 1195-1199, vol. 19.
Caterina et al., "Impaired Nociception and Pain Sensation in Mice Lacking the Capsaicin Receptor," Science, 2000, 306-313, vol. 288.
Caterina et al., "The Vanilloid Receptor: A Molecular Gateway to the Pain Pathway," Annu Rev Neurosci, 2001, 487-517, vol. 24.
Caterina M.J. et al., "The Capsaicin Receptor: A Heat-Activated Ion Channel in the Pain Pathway," (Binary/Image), 1997, 816-824, vol. 389.
Collier et al., "The abdominal constriction response and its suppression by analgesic drugs in the mouse," Br J Pharmac Chemother, 1968, 295-310, vol. 32.

(Continued)

Primary Examiner — Kamal Saeed
(74) Attorney, Agent, or Firm — Lisa V. Mueller; Michael Best & Friedrich LLP

(57) ABSTRACT

The invention discloses compounds of formula II:

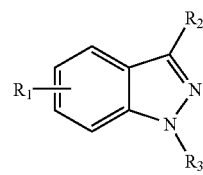

and methods of making the compounds, which are $VR_1$ antagonists that are useful in treating pain, inflammatory thermal hyperalgesia, urinary incontinence and bladder overactivity.

9 Claims, No Drawings

OTHER PUBLICATIONS

Craig, J. et al., "Derivatives of aminoisoquinolines," J.Am.Chem Soc. 1942, 783-784, vol. 64.

Davies "Indazole Derivatives: The synthesis of various amino- and hydroxy-indazoles and derived sulphonic acids," J.Chem.Soc, 1955, 2412-2423.

Davis et al., "Vanilloid receptor-1 is essential for inflammatory thermal hyperalgesia," (Binary/Image), 2000, 183-187, vol. 405.

Drizin, et al., "Structure-activity studies of a novel series of 5,6-fused heteroaromatic ureas as TRPV1 antagonists," Bioorganic & Med Chem 2006, 4740-4749, vol. 14.

Ettmayer, Peter "Lessons Learned from Marketed and Investigational Prodrugs", Medicinal Chemistry, 2004, vol. 47—Issue 10, 2394-2404.

Fieser et al., "A comparison of heterocyclic systems with benzene VI Quinines of the quinoline and isoquinoline series," J .Amer.Chem. Soc. 1935, 1840-1844, vol. 57.

Forbes I.T. et al., "N-(1-methyl-5-indolyl)-N'-(3-pyridyl)urea hydrochloride: the first selective 5-HTsub1c receptor antagonist," J.Med. Chem, 1993, 1104-1107, vol. 36.

Fowler, C. "Intravesical Treatment of Overactive Bladder," Urology, 2000, 60-64, vol. 55.

Gall, et al., "171 On a few derivatives of heterocyclic carbonic acids IV Metal ions and biological action, 36th report," Helv Chinn Acta, 1954, 90-94, vol. 37.

Gall, et al., "On a few derivatives of heterocyclic carbonic acids IV Metal ions and biological action, 36supth report" Helv Chim Acta, 1955, 1421-1423, vol. 38—Issue 171.

Giencke, et al, "Desmethyl(trifluormethyl)actinomycine," Liebigs Ann Chem, 1990, 569-579, vol. 6.

Greene, T.W. et al., "Protective Groups in Organic Synthesis", 1999, 3 rd Ed, 494-653.

Hayes et al., "Cloning and Functional Expression of a Human Orthologue of Rat Vanilloid Receptor-1," (Binary/Image), 2000, 205-215, vol. 88.

Honma Teruki, et al., "Structure-Based Generation of a New Class of Potent Cdk4 Inhibitors: New de Novo Design Strategy and Library Design," Journal of Medicinal Chemistry, 2001, 4615-4627, vol. 44, American Chemical Society.

International Search Report for application No. PCT/US07/066605, Mailed on Feb. 10, 2008, 1 page.

International Search Report, European Patent Office (Dec. 20, 2007).

Kawasaki, et al., "A new approach to 4-(2-aminoethyl)indoles via Claisen ortho-amide rearrangement of 3-hydroxy-2-methoxyindolines," J.Chem.Soc.Chem.Commun., 1990, 781-782, vol. 10.

Kumar, et al., "Antiparasitic agents: Part XV—synthesis of 2-substituted 1(3)H-imidazo[4,5-function]isoquinolines as anthelmintic agents," Indian Journal of Chemistry, 1992, 177-182, vol. 31B.

Landsiedel-Maier, D. "Structure Activity Relationship of Homonchiral 7-Substituted 1-Aminoindans as 5-HT1A Receptor Ligands, XP002296522," Archie Der Pharmazie, 1998, 59-71, vol. 331.

Lichtenthaler, et al., "Nucleosides 44 Benzo-separated Pyrazolopyrimidines: Expeditions Synthesis of [3,4-g] and [3,4-h]-linked Pyrazoloquinazolinones," Tetrahedron Letters, 1981, 4397-4400, vol. 22—Issue 44.

Lila, et al., "Large scale preparation of protected 4-aminomethylbenzamidine Application to the synthesis of the thrombin inhibitor, melagatran," Synth Comm, 1998, 4419-4429, vol. 28.

Mooney et al., "Potential antitumor agens, 10 Synthesis and biochemical properties of 5-N-alkylamino-,N,N-dialkylamino-, and N-alkylacetamido-1-formylisoquinoline thiosemicarbazones," Journal of Medicinal Chemistry, 1974, 1145-1150, vol. 17—Issue 11.

Mukkala et al., "124. New Heteroaromatic Complexing Agents and Luminescence of Their Europium(III) and Terbium(III) Chelates," Helvetica Chima Acta, 1992, 1621-1632, vol. 75.

Naruto et al., "Photo-induced Friedel-Crafts reactions IV Indoleacetic acids," Chemical and Pharmaceutical Bulletin, 1972, 2163-2171, vol. 20—Issue 10.

Nolano et al., "Topical Capsaicin in Humans: Parallel Loss of Epidermal Nerve Fibers and Pain Sensation," (Binary/Image), 1999, 135-145, vol. 81.

Nunn et al., "Semmler-Wolf Aromatization and Abnormal Beckmann and Schmidt Reactions of 3-Alkyl-4Oxo-1-phenyl-4,5,6,7,-tetrahydroindazoles and their oximes in polyphosphoric acid," J.Chem.Soc., 1973, 2697-2703, vol. 1—Issue 22, Perkin Transactions 1.

Nussbaumer, et al., "Synthesis and Structure-Activity Relationships of Side-Chain-Substituted Analogs of the Allylamine Antimycotic Terbinafine Lacking the Central Amino Function," J.Med.Chem. 1995, 1831-1836, vol. 38—Issue 10.

Perner, Richard J. et al., "In vitro structure-activity relationship and in vivo characterization of 1-(aryl)-3-(4-(amino)benzyl)urea transient receptor potential vanilloid 1 antagonists, CODEN: JMCMAR; ISSN: 0022-2623, 2007, XP002461103," Journal of Medi.

Pircio, A.W. et al., "A New Method for the Evaluation of Analgesic Activity Using Adjuvant-Induced Arthritis in the Rat," Eur Journal of Pharmacology, 1975, 207-215, vol. 31.

Poste et al., "Lipid Vesicles as Carriers for Introducing Biologically Active Materials into Cells," Methods in Cell Biology, 1976, 33-71, Chapter 4, vol. 14, Academic Press.

Prescott, et al., "Lipid Vesicles as Carriers for Introducing Biologically Active Materials into Cells," Methods in Cell Biology, 1976, 33-71, vol. 14, Academic Press.

Prijs et al., "9 On a few derivatives of heterocyclic carbonic acids I Metal ions and biological action, 16supth report," Helv Chim Acta, 1954, 90-94, vol. 37.

Remington, Joseph P. "The Science and Practice of Pharmacy", 2000, 20th Ed, 218-220.

Roe et al., "The preparation of heterocyclic fluorine compounds by the schiemann reaction III Some monofluoroisoquinolines," J. Am Chem Soc 1951, 687-689, vol. 73.

Sato, K. et al., "Construction of optically pure tryptophans from serine derived aziridine-2-carboxylates," Tetrahedro Letters, 1989, 4073-4076, vol. 30—Issue 31.

Singer Ra, "Development of nonproprietary phosphine ligands for the Pd-catalyzed amination reaction", Tetrahedron Letters, 2006, 47, 3727-3731.

Stella, Valentino J. "Expert Opinion of Therapeutic Patents", Prodrugs as therapeutics, 2004, vol. 14—Issue 3, 277-280.

Sterling J., "Novel Dual Inhibitors of AChE and MAO Derived from Hydroxy Aminoindan and Phenethylamine as Potential Treatment for Alzheimer"s Disease," Journal of Medicinal Chemistry, 2002, 5260-5279, vol. 45—Issue 24.

Taurins et al., "Thiazoloisoquinolines IV the synthesis and spectra of thiazolo[4,5-h]- and thiazolo[5,4-f]isoquinolines the ultraviolet and proton magnetic resonance spectra of some substitute isoquinolines," Canadian Journal of Chemistry, 1971, 4054-4064, vol. 49—Issue 24.

Testa, Bernard "Prodrug Research: futile or fertile?", Biochemical Pharmacology, 2004, vol. 68, 2097-2106.

Thummel R.P. et al., "Polyaza Cavity-Shaped Molecules Annelated Derivatives of 2-(2'Pyridyl)-1,8-naphthyridine and 2,2'-Bi-1,8-naphthyridine," J.Org.Chem. 1984, 2208-2212, vol. 49.

Warpehoski M. et al., "Stereoelectronic Factors Influencing the Biological Activity and Dna Interaction of Synthetic Antitumor Agents Modeled on Cc-1065," Journal of Medicianl Chemistry, 1988, 590-603, vol. 31.

Wolff "Burger's Medicinal Chemistry", 1994, 5th Ed, vol. 1, 975-977.

Lukin, K. et al., "New Practical Synthesis of Indazoles via Condensation of o-Fluorobenzaldehydes and Their O-methyloximes with Hydrazine," The Journal of Organic Chemistry, 2006, vol. 71, pp. 8166-8172.

International Search Report from International Patent Application Publication No. WO2009/117626, dated Oct. 30, 2009.

METHODS FOR MAKING CENTRAL NERVOUS SYSTEM AGENTS THAT ARE TRPV1 ANTAGONISTS

RELATED APPLICATIONS

Present application seeks priority from U.S. Provisional application 61/038,212, filed on Mar. 20, 2008, which is incorporated herein by reference in its entirety.

TECHNICAL BACKGROUND

The present invention relates to methods of making compounds that are useful for treating disorders caused by or exacerbated by vanilloid receptor activity, such as pain, bladder overactivity, and urinary incontinence.

BACKGROUND OF INVENTION

Nociceptors are primary sensory afferent (C and Aδ fibers) neurons that are activated by a wide variety of noxious stimuli including chemical, mechanical, thermal, and proton (pH <6) modalities. The lipophilic vanilloid, capsaicin, activates primary sensory fibers via a specific cell surface capsaicin receptor, cloned as $VR_1$. The intradermal administration of capsaicin is characterized by an initial burning or hot sensation followed by a prolonged period of analgesia. The analgesic component of $VR_1$ receptor activation is thought to be mediated by a capsaicin-induced desensitization of the primary sensory afferent terminal. Thus, the long lasting anti-nociceptive effects of capsaicin has prompted the clinical use of capsaicin analogs as analgesic agents. Further, capsazepine, a capsaicin receptor antagonist can reduce inflammation-induced hyperalgesia in animal models. $VR_1$ receptors are also localized on sensory afferents which innervate the bladder. Capsaicin or resiniferatoxin has been shown to ameliorate incontinence symptoms upon injection into the bladder.

The $VR_1$ receptor has been called a "polymodal detector" of noxious stimuli since it can be activated in several ways. The receptor channel is activated by capsaicin and other vanilloids and thus is classified as a ligand-gated ion channel. $VR_1$ receptor activation by capsaicin can be blocked by the competitive $VR_1$ receptor antagonist, capsazepine. The channel can also be activated by protons. Under mildly acidic conditions (pH 6-7), the affinity of capsaicin for the receptor is increased, whereas at pH less than 6, direct activation of the channel occurs. In addition, when membrane temperature reaches 43° C., the channel is opened. Thus heat can directly gate the channel in the absence of ligand. The capsaicin analog, capsazepine, which is a competitive antagonist of capsaicin, blocks activation of the channel in response to capsaicin, acid, or heat.

The channel is a nonspecific cation conductor. Both extracellular sodium and calcium enter through the channel pore, resulting in cell membrane depolarization. This depolarization increases neuronal excitability, leading to action potential firing and transmission of a noxious nerve impulse to the spinal cord. In addition, depolarization of the peripheral terminal can lead to release of inflammatory peptides such as, but not limited to, substance P and CGRP, leading to enhanced peripheral sensitization of tissue.

Recently, two groups have reported the generation of a "knock-out" mouse lacking the $VR_1$ receptor. Electrophysiological studies of sensory neurons (dorsal root ganglia) from these animals revealed a marked absence of responses evoked by noxious stimuli including capsaicin, heat, and reduced pH. These animals did not display any overt signs of behavioral impairment and showed no differences in responses to acute non-noxious thermal and mechanical stimulation relative to wild-type mice. The $VR_1$ (−/−) mice also did not show reduced sensitivity to nerve injury-induced mechanical or thermal nociception. However, the $VR_1$ knock-out mice were insensitive to the noxious effects of intradermal capsaicin, exposure to intense heat (50-55° C.), and failed to develop thermal hyperalgesia following the intradermal administration of carrageenan.

SUMMARY OF THE PRESENT INVENTION

In a first aspect, the invention is directed to methods of making compound of formula (II)

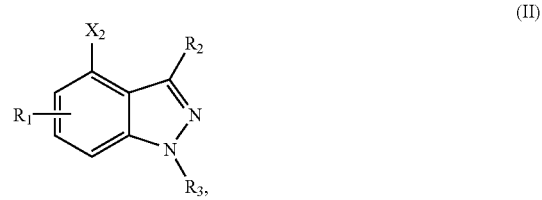

or a salt thereof, comprising reacting a compound of formula (I)

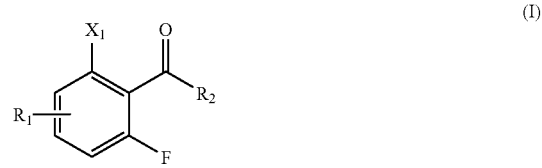

with a compound for formula (III)

wherein $X_1$ and $X_2$ are independently selected from the group consisting of: halogen, hydroxyl and alkoxy;

wherein the compound of formula II includes at least one $R_1$ group;

wherein $R_1$ may be present more than once on the indicated ring;

wherein each $R_1$ is independently selected from the group consisting of: hydrogen, hydroxyl, alkoxy, amino, substituted amino, substituted sulfur, halogen, aryl, substituted aryl, heteroaryl, substituted heteroaryl, heterocyclic, substituted heterocyclic, $C_1$-$C_8$ alkyl, $C_2$-$C_8$ alkenyl, $C_2$-$C_8$ alkynyl, substituted $C_1$-$C_8$ alkyl, substituted $C_2$-$C_8$ alkenyl, substituted —$C_2$-$C_8$ alkynyl; —$C_3$-$C_{12}$ cycloalkyl, substituted —$C_3$-$C_{12}$ cycloalkyl, —$C_3$-$C_{12}$ cycloalkenyl, and substituted —$C_3$-$C_{12}$ cycloalkenyl; each containing 0, 1, 2, or 3 heteroatoms selected from the group consisting of: O, S, and N;

$R_2$ is selected from the group consisting of: hydrogen, alkyl, and aryl;

$R_3$ is selected from the group consisting of: hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl; —$C_3$-$C_{12}$ cycloalkyl, substituted —$C_3$-$C_{12}$ cycloalkyl, —$C_3$-$C_{12}$ cycloalkenyl, and substituted —$C_3$-$C_{12}$ cycloalkenyl; each containing 0, 1, 2, or 3 heteroatoms selected from the group consisting of: O, S, and N.

In some embodiments, at least one of $X_1$ and $X_2$ is Br or Cl. In other embodiments, $R_3$ is alkyl or hydrogen, and in yet other embodiments, at least one of $X_1$ and $X_2$ is $C_1$ and $R_3$ is hydrogen or methyl.

In other embodiments, the compound of formula (I) is reacted with a compound of formula (III) in the presence of a base, such as potassium acetate, potassium carbonate, potassium bicarbonate, sodium carbonate, sodium bicarbonate, cesium carbonate, potassium phosphate tribasic, potassium phosphate dibasic, sodium phosphate dibasic, and excess compound of formula (III).

In a second aspect, the invention is directed to methods of making a compound of formula XXIV,

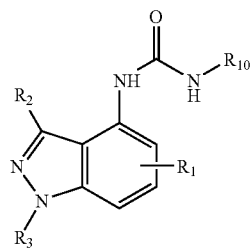
(XXIV)

or salt thereof, comprising:
reacting a compound of formula XII, $R_{10}$—CN (XII)

or $R_{10}$—$NH_2$ (XIIa)

with hydrogen in the presence of Ra—Ni, and an acid HX, preferably succinic acid, to produce a compound of formula XIII or XIIIa,

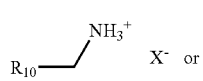
(XIII)

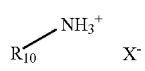
(XIIIa)

wherein preferably $X^-$ is

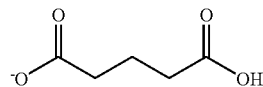

reacting the freebase of compound of formula XIII or XIIIa with $PhOCONH_2$ in the presence of a first base and a first solvent, to produce a compound of formula IV,

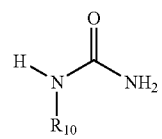
(IV)

optionally, reacting a compound of formula XII or XIIa, $R_{10}$—CN (XII)

or $R_{10}$—$NH_2$ (XIIa)

with $PhOCONH_2$ in the presence of a first base and a first solvent, to produce a compound of formula IV,

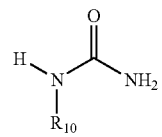
(IV)

or further optionally reacting a compound of formula XII or XIIa, in situ, $R_{10}$—CN (XII)

or $R_{10}$—$NH_2$ (XIIa)

with hydrogen in the presence of Ra—Ni, and an acid HX, and $PhOCONH_2$ in the presence of a first base and a first solvent, to produce a compound of formula IV,

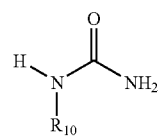
(IV)

and further reacting the compound of formula IV with a compound of formula II

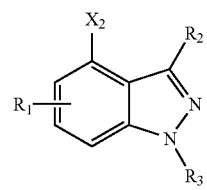
(II)

in the presence of a palladium catalyst, a second base, a second solvent, and a ligand,
wherein $X_2$ is halogen or sulfonate, wherein the sulfonate is independently substituted with fluorine or $C_1$-$C_8$ fluorinated alkanes;
wherein the compound of formula II includes at least one $R_1$ group;

wherein $R_1$ may be present more than once on the indicated ring;

wherein each wherein each $R_1$ is independently selected from the group consisting of: hydrogen, hydroxyl, alkoxy, amino, substituted amino, substituted sulfur, halogen, aryl, substituted aryl, heteroaryl, substituted heteroaryl, heterocyclic, substituted heterocyclic, $C_1$-$C_8$ alkyl, $C_2$-$C_8$ alkenyl, $C_2$-$C_8$ alkynyl, substituted $C_1$-$C_8$ alkyl, substituted $C_2$-$C_8$ alkenyl, substituted —$C_2$-$C_8$ alkynyl; —$C_3$-$C_{12}$ cycloalkyl, substituted —$C_3$-$C_{12}$ cycloalkyl, —$C_3$-$C_{12}$ cycloalkenyl, and substituted —$C_3$-$C_{12}$ cycloalkenyl; each containing 0, 1, 2, or 3 heteroatoms selected from the group consisting of: O, S, and N;

$R_2$ is selected from the group consisting of: hydrogen, alkyl, and aryl;

$R_3$ is selected from the group consisting of: hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl; —$C_3$-$C_{12}$ cycloalkyl, substituted —$C_3$-$C_{12}$ cycloalkyl, —$C_3$-$C_{12}$ cycloalkenyl, and substituted —$C_3$-$C_{12}$ cycloalkenyl; each containing 0, 1, 2, or 3 heteroatoms selected from the group consisting of: O, S, and N; and $R_{10}$ is selected from the group consisting of: aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl; —$C_3$-$C_{12}$ cycloalkyl, substituted —$C_3$-$C_{12}$ cycloalkyl, —$C_3$-$C_{12}$ cycloalkenyl, and substituted —$C_3$-$C_{12}$ cycloalkenyl; each containing 0, 1, 2, or 3 heteroatoms selected from the group consisting of: O, S, and N.

In some embodiments, $X_2$ is $C_1$, $R_3$ is hydrogen or methyl, and $R_{10}$ is aryl or alkyl; in yet other aspects, $R_{10}$ is a group of formula VIII or VIIIa

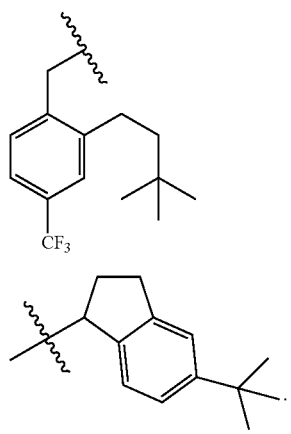

(VIII)

(VIIIa)

The first base can be N,N-diisopropyl ethyl amine, and the second base can be potassium phosphate tribasic; the first solvent can be Me-THF, and the second solvent can be DME; and the palladium catalyst is selected from the group consisting of: $Pd_2(dba)_3$, $Pd_2Cl_2(dba)$, $Pd(OAc)_2$, $Pd(OTFA)_2$, $PdCl_2$, $PdCl_2(CH_3CN)_2$, and $PdCl_2(PhCN)_2$. In some particular embodiments, the palladium catalyst is $Pd_2dba_3$.

In some embodiments, the ligand is selected from the group consisting of the compounds of formulas XXX, XXXI, XXXII, XXXIII, XXXIV, XXXV, XXXVI, XXXVII, XXXVIII, XXXIX, XL, VII:

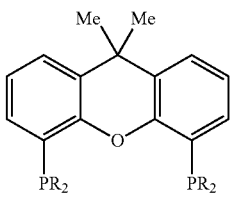

(XXX) R = Ph
(XXXI) R = 3,5-($CF_3$)$_2$Ph

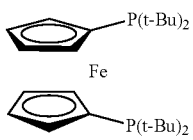

(XXXII)

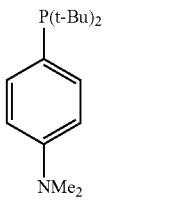

(XXXIII)

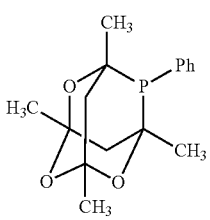

(XXXIV)

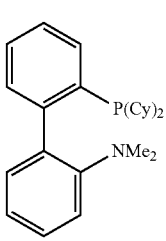

(XXXV)

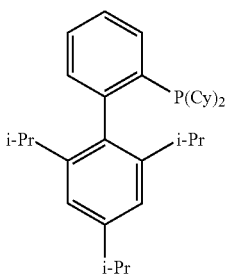

(XXXVI)

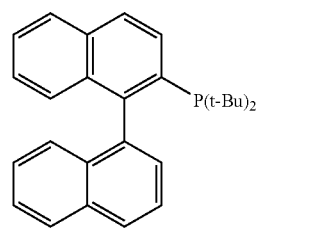
(XXXVII)
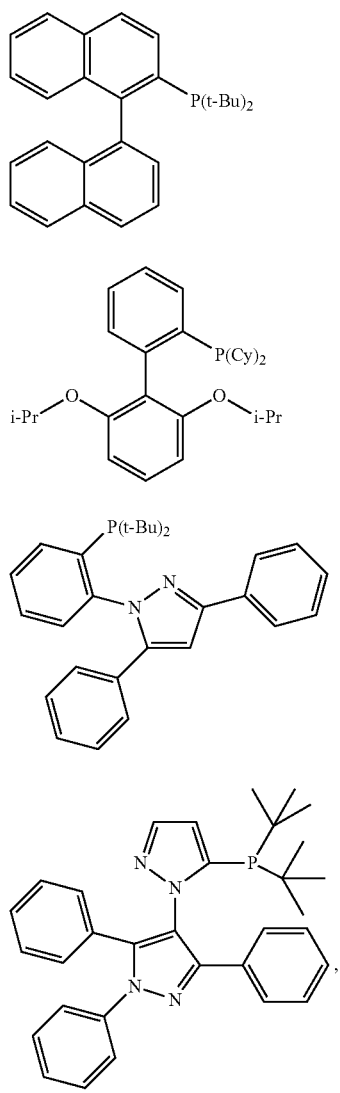
(XXXVIII)
(XXXIX)
(VII)
PdCl$_2$(dppf), and PdCl$_2$(dppf)CH$_2$Cl$_2$. In some aspects, the ligand is a compound of formula VII.
In a third aspect, the invention is directed to methods of producing a compound of formula XXIII or XXIIIa
(XXIII)
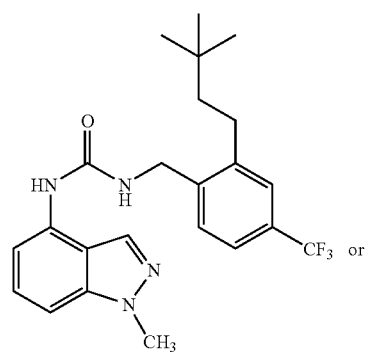
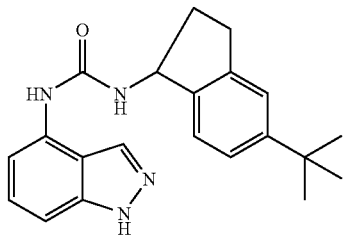
XXIIIa
or salt thereof, comprising reacting a compound of formula XX or XXa
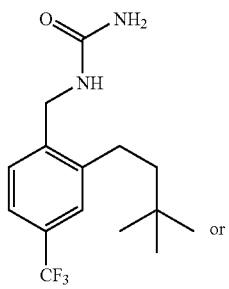
(XX)
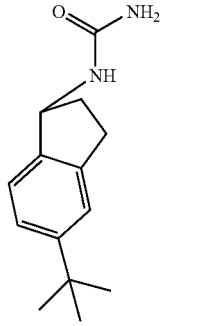
(XXa)
with a compound of formula XXII or XXIIa
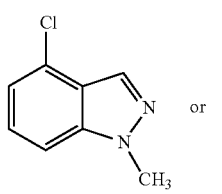
(XXII)
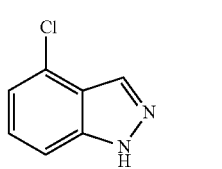
(XXIIa)

in the presence of a base, a solvent, a palladium catalyst, and a ligand of formula VII

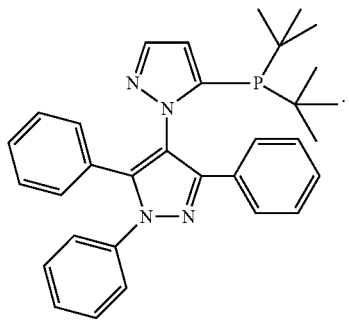
(VII)

The base can be potassium phosphate tribasic, the solvent DME, and the palladium catalyst, Pd$_2$dba$_3$.

In a fourth aspect, the invention is directed to a compound of formula XIX or XIXa:

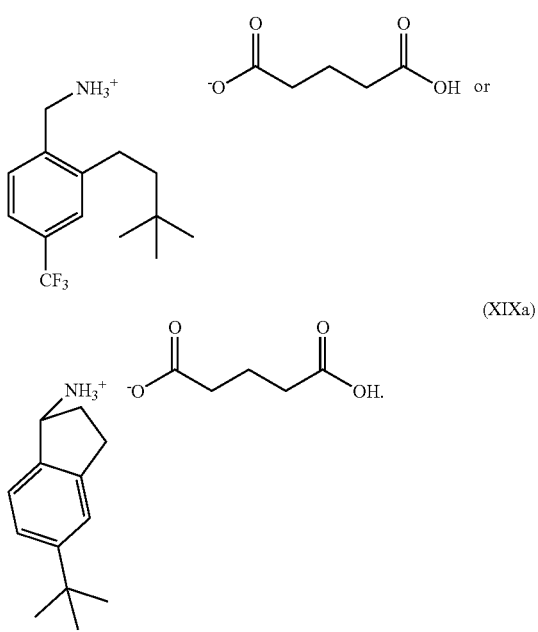
(XIX)

(XIXa)

In a fifth aspect, the invention is directed to compounds of formula XX or XXa:

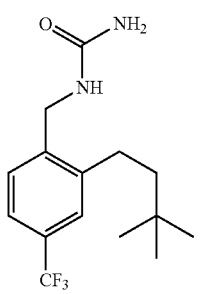
(XX)

or

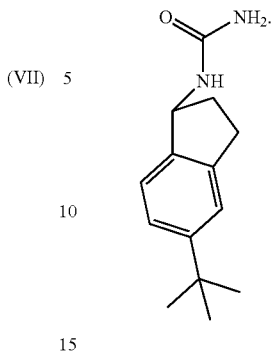
(XXa)

DETAILED DESCRIPTION OF THE PRESENT INVENTION

The invention is directed to methods of making TRPV1 antagonists that use novel syntheses, including the production of N-1 substituted indazoles, by reacting ortho-substituted aryl carboxaldehydes with hydrazine derivatives. Furthermore, the invention is directed to methods of coupling aryl chlorides with ureas using specific catalysts in the reaction to generate N-aryl ureas. Previously, a different catalyst with a very specific substrate was used in aryl chloride-urea couplings (Abad et al. (2005) *Synthesis*, 915).

In a first embodiment, the invention is directed to the synthesis of a compound of formula II as described in Scheme 1. In general, a compound of formula I is reacted with a compound of formula III in the presence of a base to produce a compound of formula II.

Scheme 1

In Scheme 1:

$X_1$ is selected from the group consisting of: halogen, hydroxyl and alkoxy;

$X_2$ is selected from the group consisting of: halogen and sulfonate, wherein the sulfonate is independently substituted with fluorine or —C$_1$-C$_8$ fluorinated alkanes;

$R_1$ may be present more than once on the indicated ring;

each $R_1$ is independently selected from the group consisting of: hydrogen, hydroxyl, alkoxy, amino, substituted amino, substituted sulfur, oxygen, nitrogen, sulfur, halogen, aryl, substituted aryl, heteroaryl, substituted heteroaryl, heterocyclic, substituted heterocyclic, —C$_1$-C$_8$ alkyl, —C$_2$-C$_8$ alkenyl, —C$_2$-C$_8$ alkynyl, substituted —C$_1$-C$_8$ alkyl, substituted —C$_2$-C$_8$ alkenyl, substituted —C$_2$-C$_8$ alkynyl; —C$_3$-C$_{12}$ cycloalkyl, substituted —C$_3$-C$_{12}$ cycloalkyl, —C$_3$-C$_{12}$ cycloalkenyl, substituted —C$_3$-C$_{12}$ cycloalkenyl; each containing 0, 1, 2, or 3 heteroatoms selected from the group consisting of: O, S, and N; and —B—R$_7$, where B is (CO), (CO)O, (CO)NR$_8$, (SO), (SO$_2$), (SO$_2$)NR$_8$; wherein R$_7$ and R$_8$ are independently selected from the group consisting of:

hydrogen, oxygen, nitrogen, sulfur, halogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl; —$C_3$-$C_{12}$ cycloalkyl, substituted —$C_3$-$C_{12}$ cycloalkyl, —$C_3$-$C_{12}$ cycloalkenyl, and substituted —$C_3$-$C_{12}$ cycloalkenyl; each containing 0, 1, 2, or 3 heteroatoms selected from the group consisting of: O, S, and N;

alternatively, $R_1$ is a group of formula IX:

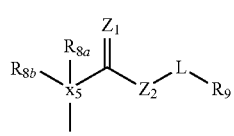

(IX)

wherein $X_5$ is selected from the group consisting of: N and C;
$Z_1$ is selected from the group consisting of: O, NH, and S;
$Z_2$ is a bond or selected from the group consisting of: NH and O;
L is selected from the group consisting of: bond, alkenylene, alkylene, alkynylene, cycloalkylene,

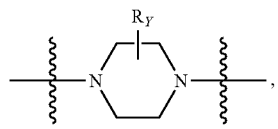

—$(CH_2)_mO(CH_2)_n$—, and $N(R_Y)$, wherein the left end of —$(CH_2)_mO(CH_2)_n$— is attached to $Z_2$ and the right end is attached to $R_9$;
m and n are each independently 0-6;
$R_Y$ is selected from the group consisting of: hydrogen and alkyl;
$R_{8a}$ is selected from the group consisting of: hydrogen and alkyl;
$R_{8b}$ is absent when $X_5$ is N or $R_{8b}$ is selected from the group consisting of: hydrogen, alkoxy, alkoxycarbonylalkyl, alkyl, alkylcarbonyloxy, alkylsulfonyloxy, halogen, and hydroxy when $X_5$ is C;
$R_2$ is selected from the group consisting of: hydrogen, alkyl, and aryl;
$R_3$ is selected from the group consisting of: hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl; —$C_3$-$C_{12}$ cycloalkyl, substituted —$C_3$-$C_{12}$ cycloalkyl, —$C_3$-$C_{12}$ cycloalkenyl, substituted —$C_3$-$C_{12}$ cycloalkenyl; each containing 0, 1, 2, or 3 heteroatoms selected from the group consisting of: O, S, and N; and —B—$R_7$, where B is (CO), (CO)O, (CO)$NR_8$, (SO), (SO$_2$), (SO$_2$)$NR_8$; wherein $R_7$ and $R_8$ are independently selected from the group consisting of: hydrogen, oxygen, nitrogen, sulfur, halogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl; —$C_3$-$C_{12}$ cycloalkyl, substituted —$C_3$-$C_{12}$ cycloalkyl, —$C_3$-$C_{12}$ cycloalkenyl, and substituted —$C_3$-$C_{12}$ cycloalkenyl; each containing 0, 1, 2, or 3 heteroatoms selected from the group consisting of: O, S, and N.

The base can be any appropriate base, such as potassium acetate, potassium carbonate, potassium bicarbonate, sodium carbonate, sodium bicarbonate, cesium carbonate, potassium phosphate tribasic, potassium phosphate dibasic, sodium phosphate dibasic, or excess compound III itself. Any suitable temperature can be used, such as between approximately 50° C. and 100° C., and such as 50, 55, 60, 65, 70, 75, 80, 85, 90, 95 and 100° C. The solvent can be any inert solvent, such as DMSO, toluene, DME, DMF, NP, DMAC, lutidine, isoproponal or other alcoholic solvents. In one embodiment, the base is potassium carbonate, the temperature is 70° C., and the solvent is DMSO.

In another embodiment, the invention is directed to a process of making a compound of formula VI, wherein a compound of formula IV is reacted with a compound of formula V in the presence of a palladium catalyst, a base, a solvent, and a ligand, shown in Scheme 2:

Scheme 2

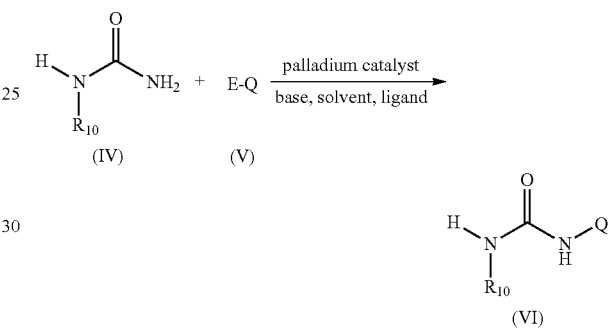

In Scheme 2:
$R_{10}$ is selected from the group consisting of: aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl; —$C_3$-$C_{12}$ cycloalkyl, substituted —$C_3$-$C_{12}$ cycloalkyl, —$C_3$-$C_{12}$ cycloalkenyl, and substituted —$C_3$-$C_{12}$ cycloalkenyl; each containing 0, 1, 2, or 3 heteroatoms selected from the group consisting of: O, S, and N;
E is a halogen;
Q is selected from the group consisting of:
an optionally substituted 6-membered heterocyclic ring, an optionally substituted 6-membered heteroaryl ring, and an optionally substituted fused bicyclic ring, wherein the optional substituents are independently selected from the group consisting of: hydrogen, oxygen, nitrogen, sulfur, halogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl; —$C_3$-$C_{12}$ cycloalkyl, substituted —$C_3$-$C_{12}$ cycloalkyl, —$C_3$-$C_{12}$ cycloalkenyl, substituted —$C_3$-$C_{12}$ cycloalkenyl; each containing 0, 1, 2, or 3 heteroatoms selected from the group consisting of: O, S, and N; and —B—$R_7$, where B is (CO), (CO)O, (CO)$NR_8$, (SO), (SO$_2$), (SO$_2$)$NR_8$; wherein $R_7$ and $R_8$ are independently selected from the group consisting of: hydrogen, oxygen, nitrogen, sulfur, halogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl; —$C_3$-$C_{12}$ cycloalkyl, substituted —$C_3$-$C_{12}$ cycloalkyl, —$C_3$-$C_{12}$ cycloalkenyl, and substituted —$C_3$-$C_{12}$ cycloalkenyl; each containing 0, 1, 2, or 3 heteroatoms selected from the group consisting of: O, S, and N;

alternatively, the optional substituents is a group of formula IX:

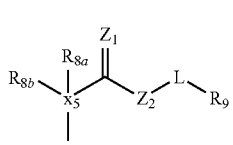
(IX)

wherein $X_5$ is selected from the group consisting of: N and C;
$Z_1$ is selected from the group consisting of: O, NH, and S;
$Z_2$ is a bond or selected from the group consisting of: NH and O;
L is selected from the group consisting of: bond, alkenylene, alkylene, alkynylene, cycloalkylene,

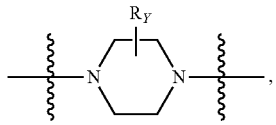

—$(CH_2)_mO(CH_2)_n$—, and $N(R_Y)$, wherein the left end of —$(CH_2)_mO(CH_2)_n$— is attached to $Z_2$ and the right end is attached to $R_9$;
m and n are each independently 0-6;
$R_Y$ is selected from the group consisting of: hydrogen and alkyl;
$R_{8a}$ is selected from the group consisting of: hydrogen and alkyl;
$R_{8b}$ is absent when $X_5$ is N or $R_{8b}$ is selected from the group consisting of: hydrogen, alkoxy, alkoxycarbonylalkyl, alkyl, alkylcarbonyloxy, alkylsulfonyloxy, halogen, and hydroxy when $X_5$ is C;
or alternatively, Q is a group of formula X:

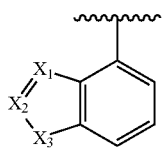
(X)

wherein
$X_1$ is selected from the group consisting of: N and $CR_4$;
$X_2$ is selected from the group consisting of: N and $CR_5$;
$X_3$ is selected from the group consisting of: N, $NR_6$, and $CR_6$;
wherein at least one of $X_1$, $X_2$, and $X_3$, is N,
wherein $R_4$, $R_5$ and $R_6$ are independently selected from the group consisting of: hydrogen, alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, carboxy, carboxyalkyl, cyano, cyanoalkyl, cycloalkyl, cycloalkylalkyl, formyl, formylalkyl, haloalkoxy, haloalkyl, haloalkylthio, halogen, hydroxy, hydroxyalkyl, mercapto, mercaptoalkyl, nitro, $(CF_3)_2(HO)C$—, —$NR_AS(O)_2R_B$, —$S(O)_2OR_A$, —$S(O)_2R_B$, —$NZ_AZ_B$, $(NZ_AZ_B)$alkyl, $(NZ_AZ_B)$carbonyl, $(NZ_AZ_B)$carbonylalkyl and $(NZ_AZ_B)$sulfonyl, wherein $Z_A$ and $Z_B$ are each independently selected from the group consisting of: hydrogen, alkyl, alkylcarbonyl, formyl, aryl, and arylalkyl.

In one embodiment, $R_{10}$ is a compound of formula VIII or VIIIa; in another embodiment, Q is a compound of formula XI or XIa. In yet another embodiment, $R_{10}$ is a compound of formula VIII or VIIIa and Q is a compound of formula XI or XIa.

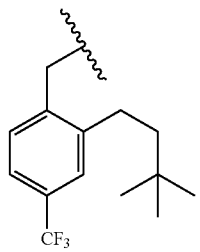
(VIII)

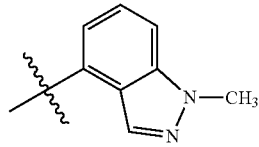
(XI)

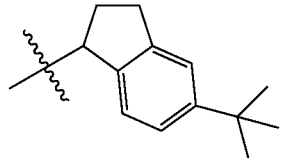
(VIIIa)

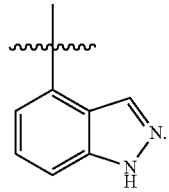
(XIa)

The base can be any appropriate base, such as sodium tert-butoxide, sodium carbonate, cesium carbonate, tribasic potassium phosphate, sodium hydroxide and potassium carbonate. In one embodiment, the base is tribasic potassium phosphate. The solvent can be chosen from inert solvents, such as DMF, DME, toluene, and mixtures thereof. In one embodiment, the solvent is DME. The reaction can be carried out at an appropriate temperature, from about 60° C. to about 100° C. In one embodiment, the reaction is carried out at about 85° C., the base is potassium phosphate tribasic, and the solvent is DME.

The palladium catalyst can be any suitable source for soluble palladium; for example, such as $Pd_2(dba)_3$, $Pd_2Cl_2(dba)$, $Pd(OAc)_2$, $Pd(OTFA)_2$, $PdCl_2$, $PdCl_2(CH_3CN)_2$, or $PdCl_2(PhCN)$. In one embodiment, the palladium catalyst is $Pd_2dba_3$.

The ligand can be precomplexed or added to the reaction mixture. The ligand can be chosen from electron-rich or bidentate classes including, but not limited to, those shown in Table 1, such as Xantphos (XXX), 3,5-bistrifluoromethyl-Xantphos (XXXI), $PdCl_2(dtbf)$ (XXXII), $PdCl_2(dppf)$, $PdCl_2(dppf)CH_2Cl_2$, Amphos (XXXIII), Adamantane (XXXIV), DavePhos (XXXV), Xphos (XXXVI), bis-tert-butyl-binaphthyl phosphine (XXXVII), RuPhos (XXXVIII), and the Bipyphos ligand of formula VII (disclosed in Singer et al. (2006) *Tetrahedron Lett.*, 47(22):3727). In one embodiment, the palladium catalyst is $Pd_2dba_3$ with Bipyphos ligand of formula VII.

TABLE 1

Examples of ligands

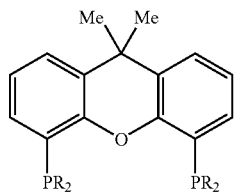

(XXX) R = Ph
(XXXI) R = 3,5-$(CF_3)_2$Ph

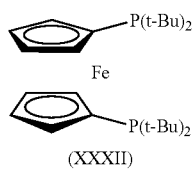

(XXXII)

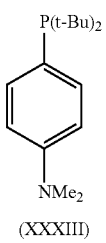

(XXXIII)

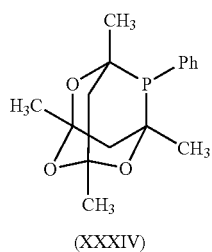

(XXXIV)

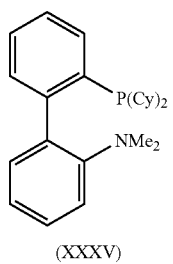

(XXXV)

TABLE 1-continued

Examples of ligands

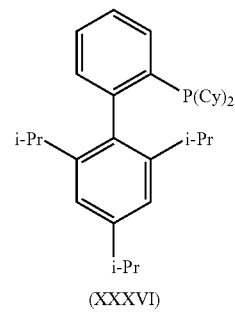

(XXXVI)

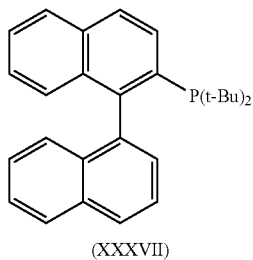

(XXXVII)

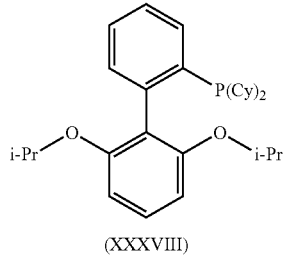

(XXXVIII)

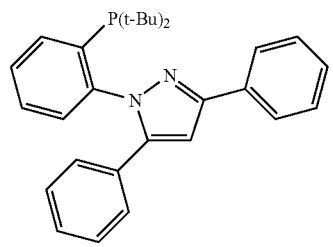

(XXXIX)

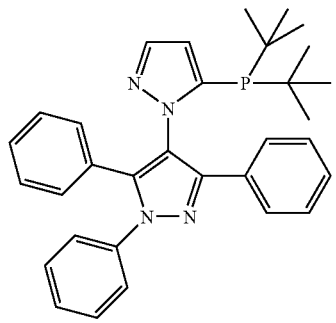

(VII)

In yet a further embodiment, the invention is directed to a process of making a compound of formula XXIV, as described in Scheme 3. In Step A, a compound of formula I is reacted with a compound of formula III in the presence of a solvent and a base to produce the compound of formula II. In a separate step, Step B, a compound of the formula XII or XIIa is reacted with hydrogen in the presence of Ra—Ni followed by succinic acid, to produce a compound of formula XIII or XIIIa. In Step 1, the freebase of the compound of formula XIII or XIIIa is reacted with PhOCONH$_2$ in the presence of a solvent and base to produce a compound of formula IV. In a final step, the compound of formula IV, produced from Steps B and 1, and the compound of formula II, produced from Step A, are reacted together in the presence of a palladium catalyst in the presence of a base, solvent, and ligand to produce the compound of formula XXIV or XXIVa.

consisting of: O, S, and N; and —B—R$_7$, where B is (CO), (CO)O, (CO)NR$_8$, (SO), (SO$_2$), (SO$_2$)NR$_8$; wherein R$_7$ and R$_8$ are independently selected from the group consisting of: hydrogen, oxygen, nitrogen, sulfur, halogen, aryl, substituted aryl, heteroaryl, substituted heteroaryl, heterocyclic, substituted heterocyclic, —C$_1$-C$_8$ alkyl, —C$_2$-C$_8$ alkenyl, —C$_2$-C$_8$ alkynyl, substituted —C$_1$-C$_8$ alkyl, substituted —C$_2$-C$_8$ alkenyl, substituted —C$_2$-C$_8$ alkynyl; —C$_3$-C$_{12}$ cycloalkyl, substituted —C$_3$-C$_{12}$ cycloalkyl, —C$_3$-C$_{12}$ cycloalkenyl, and substituted —C$_3$-C$_{12}$ cycloalkenyl; each containing 0, 1, 2, or 3 heteroatoms selected from the group consisting of: O, S, and N;

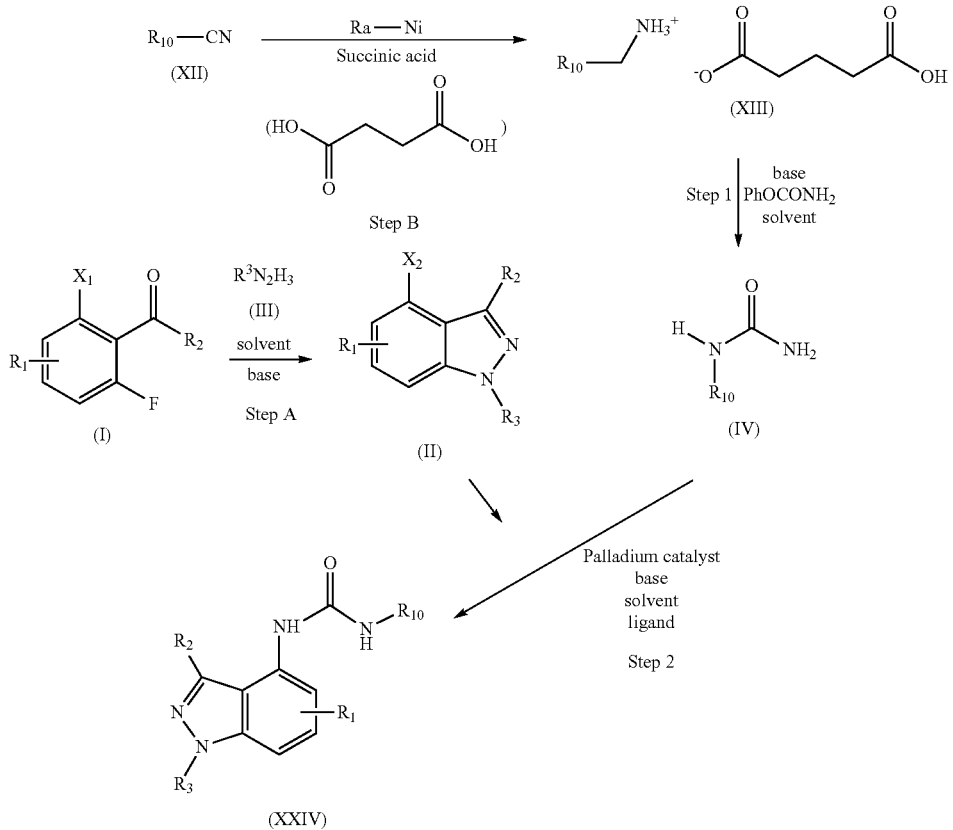

In Scheme 3:

X$_1$ is selected from the group consisting of: halogen, hydroxyl and alkoxy;

X$_2$ is selected from the group consisting of: halogen and sulfonate, wherein the sulfonate is independently substituted with fluorine or —C$_1$-C$_8$ fluorinated alkanes;

R$_1$ may be present more than once on the indicated ring;

each R$_1$ is independently selected from the group consisting of: hydrogen, hydroxyl, alkoxy, amino, substituted amino, substituted sulfur, oxygen, nitrogen, sulfur, halogen, aryl, substituted aryl, heteroaryl, substituted heteroaryl, heterocyclic, substituted heterocyclic, —C$_1$-C$_8$ alkyl, —C$_2$-C$_8$ alkenyl, —C$_2$-C$_8$ alkynyl, substituted —C$_1$-C$_8$ alkyl, substituted —C$_2$-C$_8$ alkenyl, substituted —C$_2$-C$_8$ alkynyl; —C$_3$-C$_{12}$ cycloalkyl, substituted —C$_3$-C$_{12}$ cycloalkyl, —C$_3$-C$_{12}$ cycloalkenyl, substituted —C$_3$-C$_{12}$ cycloalkenyl; each containing 0, 1, 2, or 3 heteroatoms selected from the group alternatively, R$_1$ is a group of formula IX:

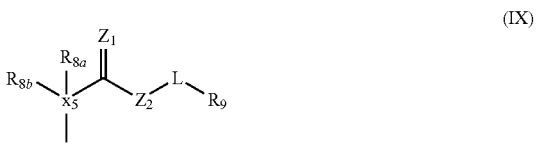

wherein X$_5$ is selected from the group consisting of: N and C;

Z$_1$ is selected from the group consisting of: O, NH, and S;

Z$_2$ is a bond or selected from the group consisting of: NH and O;

L is selected from the group consisting of: bond, alkenylene, alkylene, alkynylene, cycloalkylene,

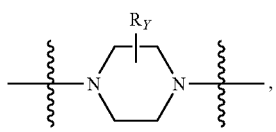

—(CH$_2$)$_m$O(CH$_2$)$_n$—, and N(R$_Y$), wherein the left end of —(CH$_2$)$_m$O(CH$_2$)$_n$— is attached to Z$_2$ and the right end is attached to R$_9$;

m and n are each independently 0-6;

R$_Y$ is selected from the group consisting of: hydrogen and alkyl;

R$_{8a}$ is selected from the group consisting of: hydrogen and alkyl;

R$_{8b}$ is absent when X$_5$ is N or R$_{8b}$ is selected from the group consisting of: hydrogen, alkoxy, alkoxycarbonylalkyl, alkyl, alkylcarbonyloxy, alkylsulfonyloxy, halogen, and hydroxy when X$_5$ is C;

R$_2$ is selected from the group consisting of: hydrogen, alkyl, and aryl;

R$_3$ is selected from the group consisting of: hydrogen, aryl, substituted aryl, heteroaryl, substituted heteroaryl, heterocyclic, substituted heterocyclic, —C$_1$-C$_8$ alkyl, —C$_2$-C$_8$ alkenyl, —C$_2$-C$_8$ alkynyl, substituted —C$_1$-C$_8$ alkyl, substituted —C$_2$-C$_8$ alkenyl, substituted —C$_2$-C$_8$ alkynyl; —C$_3$-C$_{12}$ cycloalkyl, substituted —C$_3$-C$_{12}$ cycloalkyl, —C$_3$-C$_{12}$ cycloalkenyl, substituted —C$_3$-C$_{12}$ cycloalkenyl; each containing 0, 1, 2, or 3 heteroatoms selected from the group consisting of: O, S, and N; and —B—R$_7$, where B is (CO), (CO)O, (CO)NR$_8$, (SO), (SO$_2$), (SO$_2$)NR$_8$; wherein R$_7$ and R$_8$ are independently selected from the group consisting of: hydrogen, oxygen, nitrogen, sulfur, halogen, aryl, substituted aryl, heteroaryl, substituted heteroaryl, heterocyclic, substituted heterocyclic, —C$_1$-C$_8$ alkyl, —C$_2$-C$_8$ alkenyl, —C$_2$-C$_8$ alkynyl, substituted —C$_1$-C$_8$ alkyl, substituted —C$_2$-C$_8$ alkenyl, substituted —C$_2$-C$_8$ alkynyl; —C$_3$-C$_{12}$ cycloalkyl, substituted —C$_3$-C$_{12}$ cycloalkyl, —C$_3$-C$_{12}$ cycloalkenyl, and substituted —C$_3$-C$_{12}$ cycloalkenyl; each containing 0, 1, 2, or 3 heteroatoms selected from the group consisting of: O, S, and N;

R$_{10}$ is selected from the group consisting of: aryl, substituted aryl, heteroaryl, substituted heteroaryl, heterocyclic, substituted heterocyclic, —C$_1$-C$_8$ alkyl, —C$_2$-C$_8$ alkenyl, —C$_2$-C$_8$ alkynyl, substituted —C$_1$-C$_8$ alkyl, substituted —C$_2$-C$_8$ alkenyl, substituted —C$_2$-C$_8$ alkynyl; —C$_3$-C$_{12}$ cycloalkyl, substituted —C$_3$-C$_{12}$ cycloalkyl, —C$_3$-C$_{12}$ cycloalkenyl, and substituted —C$_3$-C$_{12}$ cycloalkenyl; each containing 0, 1, 2, or 3 heteroatoms selected from the group consisting of: O, S, and N. In one embodiment, R$_{10}$ is a compound of formula VIII or VIIIa.

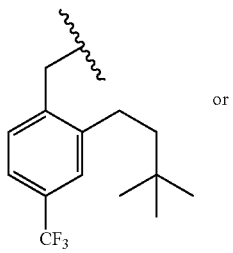

(VIII)

or

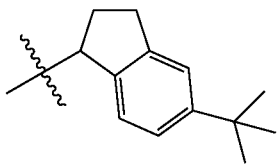

(VIIIa)

The base to freebase the amine for Step 1 can be any appropriate base, such as sodium carbonate, cesium carbonate, tribasic potassium phosphate or potassium carbonate. In one embodiment, the base to freebase the amine for Step 1 is sodium hydroxide, the base in Step 1 is N,N-diisopropyl ethyl amine, the base in Step 2 is potassium phosphate tribasic, the base in Step A is potassium carbonate, the base in Step C is triethylamine (TEA).

Any suitable solvent for each particular step can be used. In one embodiment, the solvent in Step A is DMSO, the solvent in Step 1 is Me-THF, and the solvent in Step 2 is DME. The palladium catalyst for Step 2 can be any suitable one, such as Pd$_2$(dba)$_3$, Pd$_2$Cl$_2$(dba), Pd(OAc)$_2$, Pd(OTFA)$_2$, PdCl$_2$, PdCl$_2$(CH$_3$CN)$_2$, or PdCl$_2$(PhCN)$_2$. In one embodiment, the palladium catalyst is Pd$_2$dba$_3$. The ligand can be precomplexed or added to the reaction mixture. The ligand can be chosen from electron-rich or bidentate classes including, but not limited to, those shown in Table 1, such as Xantphos (XXX), 3,5-bistrifluoromethyl-Xantphos (XXXI), PdCl$_2$ (dtbf) (XXXII), PdCl$_2$(dppf), PdCl$_2$(dppf)CH$_2$Cl$_2$, Amphos (XXXIII), Adamantane (XXXIV), DavePhos (XXXV), Xphos (XXXVI), bis-tert-butyl-binaphthyl phosphoine (XXXVII), RuPhos (XXXVIII), and the Bipyphos ligand of formula VII (disclosed in Singer et al. (2006) *Tetrahedron Lett.*, 47(22):3727). In one embodiment, the palladium catalyst is Pd$_2$dba$_3$ with Bipyphos ligand of formula VII. The steps can be carried out at an appropriate temperature for that step. In one embodiment, Step A is carried out at about 70° C., Step B is carried out at about 50° C., Step 1 is carried out at about 45° C., and Step 2 is carried out at about 80° C.

In another embodiment, the invention is directed to making a compound of formula XXIII or XXIIIa as shown in Scheme 4. Thus for example, in Step A, a compound of formula XXI is reacted with MeN$_2$H$_3$ in the presence of a solvent and in the presence of a base to produce the compound of formula XXII. In a separate step, Step C, a compound of the formula XVII is reacted with t-butylacetylene in the presence of a palladium catalyst, a base, CuI, and Davephos to produce the compound of formula XVIII. In Step B, the compound of formula XVIII is reacted with hydrogen in the presence of Ra—Ni followed by succinic acid, to produce a compound of formula XIX. In Step 1, the compound of formula XIX is reacted with PhO-CONH$_2$ in the presence of a solvent and base to produce a compound of formula XX. In a final step, the compound of formula XX, produced from Steps C, B and 1, and the compound of formula XXII, produced from Step A, are reacted together in the presence of a palladium catalyst in the presence of a base, solvent, and catalyst. Similarly compound XXIII may be made using starting materials as previously described.

The base in Step C can be any appropriate base, such as sodium carbonate, cesium carbonate, tribasic potassium phosphate and potassium carbonate, or N,N-diisopropylethyl amine. In one embodiment, the base is N,N-diisopropylethyl amine. Any suitable solvent can be used, such as DMF, DME, toluene, and mixtures thereof. In one embodiment, the solvent is 2-methyl-THF. The reaction can be carried out from about 20° C. to about 130° C. In one embodiment, the reaction is carried out at about 45° C.

The base can be any appropriate base, such as sodium carbonate, cesium carbonate, tribasic potassium phosphate, potassium carbonate, triethylamine, or N,N-diisopropylethylamine. In one embodiment, the base in Step 1 is N,N-diisopropylethylamine, the base in Step 2 is tribasic potassium phosphate, and the base in Step A is potassium carbonate. Any suitable solvent can be used for the particular step. In one embodiment, the solvent in Step A is DMSO, the solvent in Step 1 is Me-THF and the solvent in Step 2 is DME.

The palladium catalyst for Step 2 can be any suitable one, such as $Pd_2(dba)_3$, $Pd_2Cl_2(dba)$, $Pd(OAc)_2$, $Pd(OTFA)_2$, $PdCl_2$, $PdCl_2(CH_3CN)_2$, or $PdCl_2(PhCN)_2$. In one embodiment, the palladium catalyst is $Pd_2dba_3$. The steps can be carried out at an appropriate temperature for that step. In one embodiment, Step A is carried out at about 70° C., Step C is carried out at about 65° C., Step 1 is carried out at about 45° C., and Step 2 is carried out at about 80° C. The ligand can be any appropriate ligand, including Xantphos (XXX), 3,5-bis-trifluoromethyl-Xantphos (XXXI), $PdCl_2$(dtbf) (XXXII), $PdCl_2$(dppf), $PdCl_2$(dppf)$CH_2Cl_2$, Amphos (XXXIII), Adamantane (XXXIV), DavePhos (XXXV), Xphos (XXXVI), bis-tert-butyl-binaphthyl phosphine (XXXVII), RuPhos (XXXVIII), and the Bipyphos ligand of formula VII (disclosed in Singer et al. (2006) *Tetrahedron Lett.*, 47(22):3727). In one embodiment, the palladium catalyst is $Pd_2dba_3$ with Bipyphos ligand of formula VII.

Scheme 4

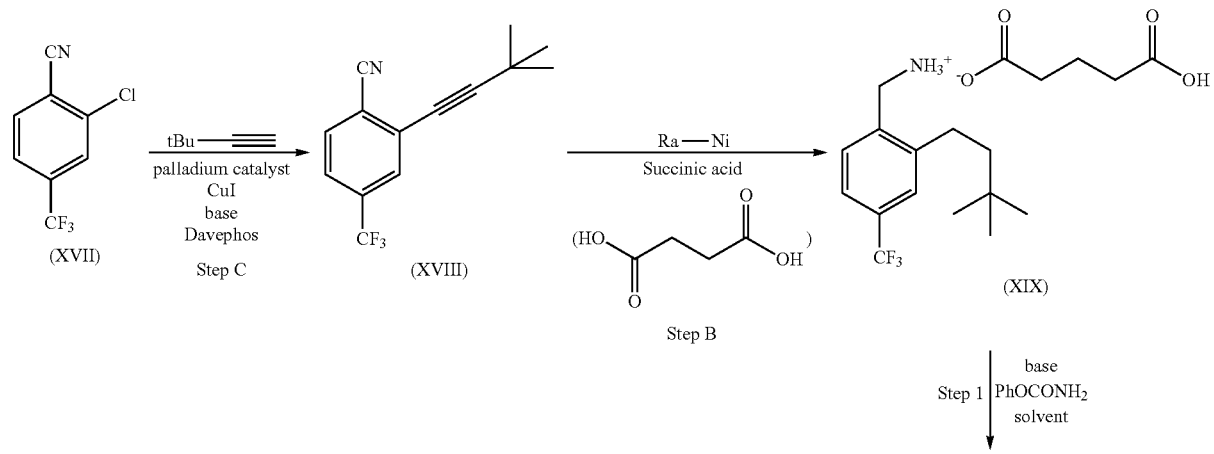

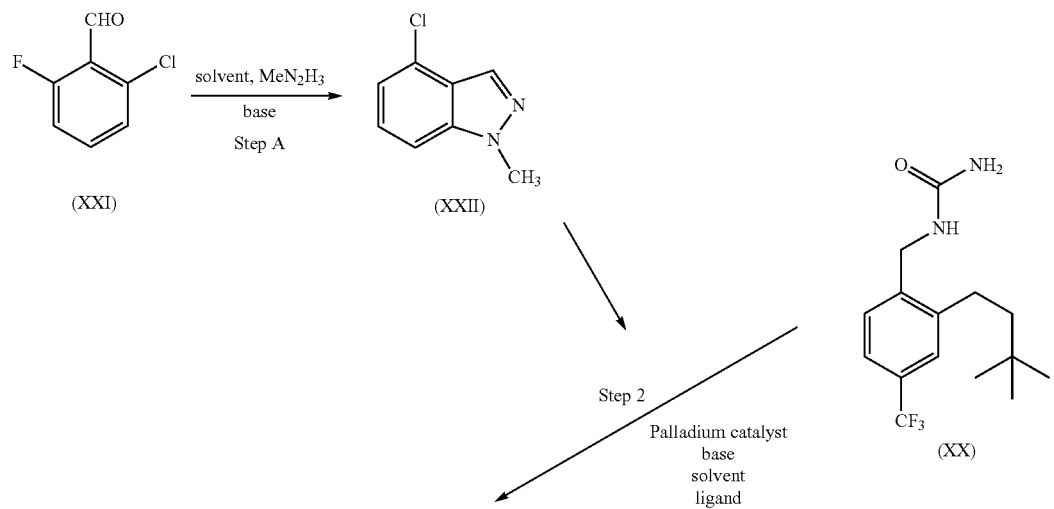

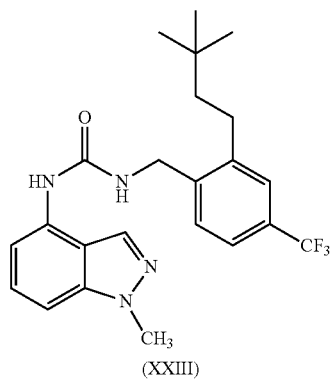

(XXIII)

In another embodiment, the invention is directed to making a compound of formula XXIII as shown in Scheme 5. A compound of formula XXV (2-bromo-6-fluorobenzaldehyde) in a solvent, such as DMSO, is added to methylhydrazine ($MeN_2H_3$) to produce the compound of formula XXVI. The compound of formula XXVI is then mixed with palladium acetate ($Pd(OAc)_2$), Xantphos and benzophenone imine ($Ph_2C=NH$), followed by sodium tert-butoxide and then HCl to produce a compound of formula XXVII (1-methyl-4-aminoindazole hydrochloride). The compound of formula XXVII is then mixed with pyridine and disuccinimidyl carbonate (XXVIII) to produce a compound of formula XXIII.

In addition to $Pd(OAc)_2$, the palladium catalyst can be any suitable one, in one embodiment, the palladium catalyst is $Pd_2dba_3$. In addition to Xantphos, the ligand can be any appropriate ligand, including (XXXIV), DavePhos (XXXV), Xphos (XXXVI), bis-tert-butyl-binaphthyl phosphine (XXXVII), RuPhos (XXXVIII).

Any suitable reaction temperatures can be any appropriate ones; for example, when adding 2-bromo-6-fluorobenzaldehyde (XXV) in DMSO to methylhydrazine, the internal temperature can be maintained at less than approximately 35° C., and then reacted at approximately 80° C. for a sufficient time to produce a compound of formula XXVI, after which the internal temperature can be adjusted to approximately 25° C. When the aqueous layer is extracted, the temperature of the mixture can be maintained at less than approximately 40° C. When reacting a compound of formula XXVI to produce a compound of formula XXVII, the temperature at which the reagents are added can be, for example, room temperature, while the reaction is carried out, for example, at approximately 80-85° C. before cooling to approximately room temperature. When reacting a compound of formula XXVII to produce a compound of formula XXIII, the reactants can be added at an internal temperature of approximately 25° C. or less, and reacted at approximately the same temperature. The compound of XXIII can then be dissolved, for example, at approximately 70° C., then precipitated at approximately 65° C.-70° C. before cooling to approximately room temperature.

Similarly compound XXIIIa may be manufactured using VIIIa and XXIV as the starting material.

Scheme 5

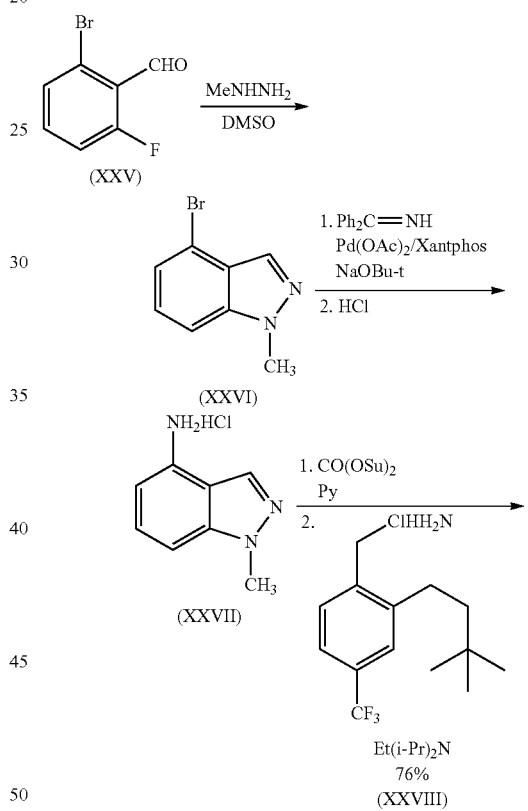

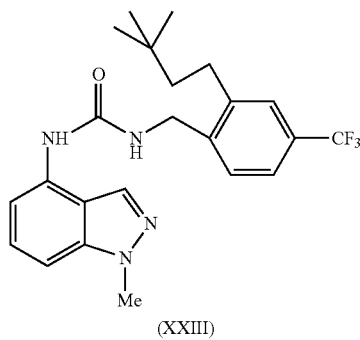

(XXIII)

DEFINITIONS

As used throughout this specification and the appended claims, the following terms have the following meanings:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of from 2 to 10 carbon atoms containing at least one double bond. Representative examples of alkenylene include, but are not limited to, —CH=CH—, —CH=CH$_2$CH$_2$—, and —CH=C(CH$_3$)CH$_2$—.

The term "alkoxy" as used herein, means an alkyl group appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein, means an alkoxy group, as defined herein, appended to the parent molecular moiety through an alkoxy group, as defined herein. Representative examples of alkoxyalkoxy include, but are not limited to, methoxymethoxy, ethoxymethoxy and 2-ethoxyethoxy.

The term "alkoxyalkyl" as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkyl group, as defined herein. Representative examples of alkoxycarbonylalkyl include, but are not limited to, 3-methoxycarbonylpropyl, 4-ethoxycarbonylbutyl, and 2-tert-butoxycarbonylethyl.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonylalkyl" as used herein, means an alkylcarbonyl group, as defined herein, appended to the parent molecular moiety through an alkyl group, as defined herein. Representative examples of alkylcarbonylalkyl include, but are not limited to, 2-oxopropyl, 3,3-dimethyl-2-oxopropyl, 3-oxobutyl, and 3-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylene" means a divalent group derived from a straight or branched chain hydrocarbon of from 1 to 10 carbon atoms. Representative examples of alkylene include, but are not limited to, —CH$_2$—, —CH$_2$CH$_2$—, —CH$_2$CH$_2$CH$_2$—, —CH$_2$CH$_2$CH$_2$CH$_2$—, —CH$_2$CH(CH$_3$)CH$_2$—, and —(CH$_2$)$_p$CH(R$_Z$)(CH$_2$)$_q$—, wherein p and q are independently 0-4 and R$_Z$ is selected from the group consisting of: aryl, cycloalkyl, and hydroxy. A preferred aryl group is phenyl.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein, means an alkyl group, as defined herein, appended to the parent molecular moiety through a sulfur atom. Representative examples of alkylthio include, but are not limited, methylsulfanyl, ethylsulfanyl, tert-butylsulfanyl, and hexylsulfanyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "alkynylene" means a divalent group derived from a straight or branched chain hydrocarbon of from 2 to 10 carbon atoms containing at least one triple bond. Representative examples of alkynylene include, but are not limited to, —C≡C—, —CH$_2$C≡C—, —CH(CH$_3$)CH$_2$C≡C—, —C≡CCH$_2$—, and —C≡CCH(CH$_3$)CH$_2$—.

The term "aryl" as used herein, means a phenyl group, or a bicyclic or a tricyclic fused ring system wherein one or more of the fused rings is a phenyl group. Bicyclic fused ring systems are exemplified by a phenyl group fused to a cycloalkyl group, as defined herein, or another phenyl group. Tricyclic fused ring systems are exemplified by a bicyclic fused ring system fused to a cycloalkyl group, as defined herein, or another phenyl group. Representative examples of aryl include, but are not limited to, anthracenyl, azulenyl, fluorenyl, indanyl, indenyl, naphthyl, phenyl and tetrahydronaphthyl.

The aryl groups of this invention can be substituted with 1, 2, 3, 4 or 5 substituents independently selected from the group consisting of: alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylsulfonyl, alkylthio, alkynyl, carboxy, carboxyalkyl, cyano, cyanoalkyl, cycloalkyl, cycloalkylalkyl, ethylenedioxy, formyl, formylalkyl, haloalkoxy, haloalkyl, haloalkylthio, halogen, hydroxy, hydroxyalkyl, methylenedioxy, mercapto, mercaptoalkyl, nitro, —NZ$_C$Z$_D$, (NZ$_C$Z$_D$)alkyl, (NZ$_C$Z$_D$)carbonyl, (NZ$_C$Z$_D$)carbonylalkyl, (NZ$_C$Z$_D$)sulfonyl, —NR$_A$S(O)$_2$R$_B$, —S(O)$_2$OR$_A$ and —S(O)$_2$R$_A$ wherein R$_A$ and R$_B$ are as defined herein. The aryl groups of this invention can be further substituted with any one of an additional aryl, arylalkyl, aryloxy, arylthio, heterocycle, heterocyclealkyl, heterocycleoxy, or heterocyclethio group, as defined herein, wherein the additional aryl, arylalkyl, aryloxy, arylthio, heterocycle, heterocyclealkyl, heterocycleoxy, and heterocyclethio group can be substituted with 1, 2, 3, 4, or 5 substituents independently selected from the group consisting of: alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylsulfonyl, alkylthio, alkynyl, carboxy, carboxyalkyl, cyano, cyanoalkyl, cycloalkyl, cycloalkylalkyl, formyl, formylalkyl, haloalkoxy, haloalkyl, haloalkylthio, halogen, hydroxy, hydroxyalkyl, mercapto, mercaptoalkyl, nitro, —$NZ_CZ_D$, ($NZ_CZ_D$)alkyl, ($NZ_CZ_D$)carbonyl, ($NZ_CZ_D$)carbonylalkyl, ($NZ_CZ_D$)sulfonyl, —$NR_AS(O)_2R_B$, —$S(O)_2OR_A$ and —$S(O)_2R_A$ wherein $R_A$ and $R_B$ are as defined herein. Representative examples include, but are not limited to, 4-(2-azabicyclo[2.2.1]hept-2-yl)-2-(trifluoromethyl)phenyl, 4-(8-azabicyclo[3.2.1]oct-8-yl)-2-chlorophenyl, 4-(8-azabicyclo[3.2.1]oct-8-yl)-3-chlorophenyl, 4-(8-azabicyclo[3.2.1]oct-8-yl)phenyl, 4-(8-azabicyclo[3.2.1]oct-8-yl)-3-(trifluoromethyl)phenyl, 4-(8-azabicyclo[3.2.1]oct-8-yl)-2-(trifluoromethyl)phenyl, 4-(8-azabicyclo[3.2.1]oct-8-yl)-3-fluorophenyl, 3-chloro-4-azepan-1-ylphenyl, 2-chloro-4-azepan-1-ylphenyl, 3,5-difluoro-4-azepan-1-ylphenyl, 4-(8-azabicyclo[3.2.1]oct-8-yl)-3,5-difluorophenyl, 4-bromophenyl, 3-chlorophenyl, 4-chlorophenyl, 3,4-dichlorophenyl, 2,3-dichlorophenyl, 2,4-dichlorophenyl, 3,5-dichlorophenyl, 3,4-difluorophenyl, 4-bromo-2-fluorophenyl, 4-chloro-2-fluorophenyl, 4-(tert-butyl)phenyl), 4-cyanophenyl, 4-ethylphenyl, 3-fluorophenyl, 2,4-difluorophenyl, 4-bromo-3-fluorophenyl, 2,3-difluoro-4-(trifluoromethyl)phenyl, 3-fluoro-4-(trifluoromethyl)phenyl, 3-fluoro-5-(trifluoromethyl)phenyl, 3-(trifluoromethyl)phenyl, 4-(trifluoromethyl)phenyl, 4-(trifluoromethoxy)phenyl, 3-(trifluoromethoxy)phenyl, 4-[(trifluoromethyl)thio]phenyl, 4-azepan-1-yl-3-(trifluoromethyl)phenyl, 4-azepan-1-yl-2-(trifluoromethyl)phenyl, 3-methylphenyl, 3,4-dimethylphenyl, 2,4-dimethylphenyl, 4-isopropylphenyl, 4-methylphenyl, 4-bromo-3-methylphenyl, 4-fluoro-3-(trifluoromethyl)phenyl, 3-chloro-4-fluorophenyl, 4-(1-pyrrolidinyl)phenyl, 4-(1-azepanyl)phenyl, 3-fluoro-4-(1-pyrrolidinyl)phenyl, 3-fluoro-4-(1-azepanyl)phenyl, 4-(1-azocanyl)phenyl, 4-(1-piperidinyl)phenyl, 3-fluoro-4-(1-piperidinyl)phenyl, 4-(2-pyridinyl)phenyl, 1,1'-biphenyl, 3-fluoro-4-(4-methyl-1-piperidinyl)phenyl, 4-(4-methyl-1-piperidinyl)phenyl, 4-(4-morpholinyl)phenyl, 4-(2,6-dimethyl-4-morpholinyl)phenyl, 4-(4-thiomorpholinyl)phenyl, 3,5-difluoro-4-(4-morpholinyl)phenyl, 3,5-bis(trifluoromethyl)phenyl, and 2,5-bis(trifluoromethyl)phenyl.

The term "arylalkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "aryloxy" as used herein, means an aryl group, as defined herein, appended to the parent molecular moiety through an oxygen atom. Representative examples of aryloxy include, but are not limited to, phenoxy, naphthyloxy, 3-bromophenoxy, 4-chlorophenoxy, 4-methylphenoxy, and 3,5-dimethoxyphenoxy.

The term "arylthio" as used herein, means an aryl group, as defined herein, appended to the parent molecular moiety through a sulfur atom. Representative examples of arylthio include, but are not limited to, phenylsulfanyl, naphth-2-ylsulfanyl, and 5-phenylhexylsulfanyl.

The term "carbonyl" as used herein, means a —C(O)— group.

The term "carboxy" as used herein, means a —$CO_2H$ group.

The term "carboxyalkyl" as used herein, means a carboxy group, as defined herein, appended to the parent molecular moiety through an alkyl group, as defined herein. Representative examples of carboxyalkyl include, but are not limited to, carboxymethyl, 2-carboxyethyl, and 3-carboxypropyl.

The term "cyano" as used herein, means a —CN group.

The term "cyanoalkyl" as used herein, means a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cycloalkyl" as used herein, means a monocyclic, bicyclic, or tricyclic ring system. Monocyclic ring systems are exemplified by a saturated cyclic hydrocarbon group containing from 3 to 12 carbon atoms. Examples of monocyclic ring systems include cyclopropyl, cyclobutyl, cyclopentyl, cyclohexyl, cycloheptyl, and cyclooctyl. Bicyclic ring systems are exemplified by a bridged monocyclic ring system in which two non-adjacent carbon atoms of the monocyclic ring are linked by an alkylene bridge of between one and three additional carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic ring systems are exemplified by a bicyclic ring system in which two non-adjacent carbon atoms of the bicyclic ring are linked by a bond or an alkylene bridge of between one and three carbon atoms. Representative examples of tricyclic-ring systems include, but are not limited to, tricyclo[3.3.1.0$^{3,7}$]nonane and tricyclo[3.3.1.1$^{3,7}$]decane (adamantyl).

The cycloalkyl groups of this invention can be substituted with 1, 2, 3, 4 or 5 substituents independently selected from the group consisting of: alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylsulfonyl, alkylthio, alkynyl, carboxy, carboxyalkyl, cyano, cyanoalkyl, formyl, haloalkoxy, haloalkyl, haloalkylthio, halogen, hydroxy, hydroxyalkyl, mercapto, mercaptoalkyl, nitro, —$NZ_CZ_D$, ($NZ_CZ_D$)alkyl, ($NZ_CZ_D$)carbonyl, ($NZ_CZ_D$)carbonylalkyl, ($NZ_CZ_D$)sulfonyl, —$NR_AS(O)_2R_B$, —$S(O)_2OR_A$, and —$S(O)_2R_A$ wherein $R_A$ and $R_B$ are as defined herein. Representative examples include, but are not limited to, 6,6-dimethylbicyclo[3.1.1]heptyl, 6,6-dimethylbicyclo[3.1.1]hept-2-yl, 4-tert-butylcyclohexyl, and 4-(trifluoromethyl)cyclohexyl.

The term "cycloalkylalkyl" as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "cycloalkylene" as used herein, means a divalent group derived from a cycloalkyl group, as defined herein. Representative examples of cycloalkylene include, but are not limited to

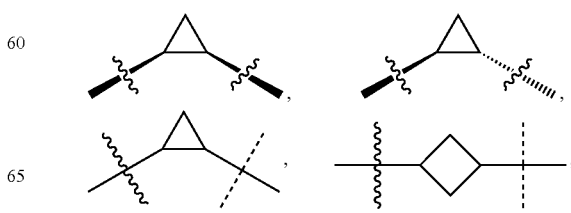

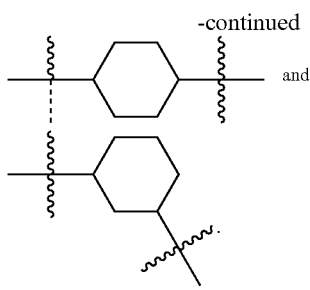

The term "ethylenedioxy" as used herein, means a —O(CH$_2$)$_2$O— group wherein the oxygen atoms of the ethylenedioxy group are attached to the parent molecular moiety through one carbon atom forming a 5 membered ring or the oxygen atoms of the ethylenedioxy group are attached to the parent molecular moiety through two adjacent carbon atoms forming a six membered ring.

The term "formyl" as used herein, means a —C(O)H group.

The term "formylalkyl" as used herein, means a formyl group, as defined herein, appended to the parent molecular moiety through an alkyl group, as defined herein. Representative examples of formylalkyl include, but are not limited to, formylmethyl and 2-formylethyl.

The term "halo" or "halogen" as used herein, means —Cl, —Br, —I or —F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, 2-chloro-3-fluoropentyloxy, and pentafluoroethoxy.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "haloalkylthio" as used herein, means at least one halogen, as defined herein, appended to the parent molecular moiety through an alkylthio group, as defined herein. Representative examples of haloalkylthio include, but are not limited to, trifluoromethylthio.

The term "heteroaryl," means a monocyclic heteroaryl or a bicyclic heteroaryl. The monocyclic heteroaryl is a 5 or 6 membered ring that contains at least one heteroatom selected from the group consisting of: nitrogen, oxygen and sulfur. The 5 membered ring contains two double bonds and the 6 membered ring contains three double bonds. The 5 or 6 membered heteroaryl is connected to the parent molecular moiety through any carbon atom or any substitutable nitrogen atom contained within the heteroaryl, provided that proper valance is maintained. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, or a monocyclic heteroaryl fused to a cycloalkyl, or a monocyclic heteroaryl fused to a cycloalkenyl, or a monocyclic heteroaryl fused to a monocyclic heteroaryl. The bicyclic heteroaryl is connected to the parent molecular moiety through any carbon atom or any substitutable nitrogen atom contained within the bicyclic heteroaryl, provided that proper valance is maintained. Representative examples of bicyclic heteroaryl include, but are not limited to, azaindolyl, benzimidazolyl, benzofuranyl, benzoxadiazolyl, benzoisoxazole, benzoisothiazole, benzooxazole, 1,3-benzothiazolyl, benzothiophenyl, cinnolinyl, furopyridine, indolyl, indazolyl, isobenzofuran, isoindolyl, isoquinolinyl, naphthyridinyl, oxazolopyridine, quinolinyl, quinoxalinyl and thienopyridinyl, The heteroaryl groups of the invention are optionally substituted with 1, 2, 3 or 4 substituents independently selected from the group consisting of: alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, formyl, haloalkoxy, haloalkyl, halogen, hydroxy, hydroxyalkyl, mercapto, nitro, —NZ$_1$Z$_2$ and (NZ$_3$Z$_4$)carbonyl. Heteroaryl groups of the invention that are substituted with a hydroxyl group may be present as tautomers. The heteroaryl groups of the invention encompasses all tautomers including non-aromatic tautomers.

The term "heterocycle" or "heterocyclic" as used herein, means a monocyclic, bicyclic, or tricyclic ring system. Monocyclic ring systems are exemplified by any 3- or 4-membered ring containing a heteroatom independently selected from the group consisting of: oxygen, nitrogen and sulfur; or a 5-, 6- or 7-membered ring containing one, two or three heteroatoms wherein the heteroatoms are independently selected from the group consisting of: nitrogen, oxygen and sulfur. The 5-membered ring has from 0-2 double bonds and the 6- and 7-membered ring have from 0-3 double bonds. Representative examples of monocyclic ring systems include, but are not limited to, azetidinyl, azepanyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridinyl, pyrimidinyl, pyridazinyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, 1,1-dioxidothiomorpholinyl (thiomorpholine sulfone), thiopyranyl, triazinyl, triazolyl, and trithianyl. Bicyclic ring systems are exemplified by any of the above monocyclic ring systems fused to an aryl group as defined herein, a cycloalkyl group as defined herein, or another monocyclic ring system. Additionally, bicyclic ring systems are exemplified by a bridged monocyclic ring system in which two non-adjacent carbon atoms of the monocyclic ring system are linked by an alkylene group. Representative examples of bicyclic ring systems include, but are not limited to, 2-azabicyclo[2.2.1]heptyl, 8-azabicyclo[3.2.1]octyl, benzimidazolyl, benzodioxinyl, benzothiazolyl, benzothienyl, benzotriazolyl, benzoxazolyl, benzofuranyl, benzopyranyl, benzothiopyranyl, cinnolinyl, indazolyl, indolyl, 2,3-dihydroindolyl, indolizinyl, naphthyridinyl, isobenzofuranyl, isobenzothienyl, isoindolyl, isoquinolinyl, phthalazinyl, pyranopyridinyl, quinolinyl, quinolizinyl, quinoxalinyl, quinazolinyl, tetrahydroisoquinolinyl, tetrahydroquinolinyl, and thiopyranopyridinyl. Tricyclic rings systems are exemplified by any of the above bicyclic ring systems fused to an aryl group as defined herein, a cycloalkyl group as defined herein, or a monocyclic ring system. Representative examples of tricyclic ring systems include, but are not limited to, acridinyl, carbazolyl, carbolinyl, dibenzo[b,d]furanyl, dibenzo[b,d]thienyl, naphtho[2,3-b]furan, naphtho[2,3-b]thienyl, phenazinyl, phenothiazinyl, phenoxazinyl, thianthrenyl, thioxanthenyl and xanthenyl.

The heterocycles of this invention can be substituted with 1, 2, or 3 substituents independently selected from the group consisting of: alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylsulfonyl, alkylthio, alkynyl, arylalkyl, aryloxy, arylthio, carboxy, carboxyalkyl, cyano, cyanoalkyl, cycloalkyl, cycloalkylalkyl, formyl, formylalkyl, haloalkoxy, haloalkyl, haloalkylthio, halogen, hydroxy, hydroxyalkyl, mercapto, mercaptoalkyl, nitro, oxo, —$NZ_CZ_D$, ($NZ_CZ_D$)alkyl, ($NZ_CZ_D$)carbonyl, ($NZ_CZ_D$)carbonylalkyl, ($NZ_CZ_D$)sulfonyl, —$NR_AS(O)_2R_B$, —$S(O)_2OR_A$ and —$S(O)_2R_A$ wherein $R_A$ and $R_B$ are as defined herein. The heterocycles of this invention can be further substituted with any one of an additional aryl, arylalkyl, aryloxy, arylthio, heterocycle, heterocyclealkyl, heterocycleoxy, or heterocyclethio group, as defined herein, wherein the additional aryl, arylalkyl, aryloxy, arylthio, heterocycle, heterocyclealkyl, heterocycleoxy, and heterocyclethio group can be substituted with 1, 2, or 3 substituents independently selected from the group consisting of: alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylsulfonyl, alkylthio, alkynyl, carboxy, carboxyalkyl, cyano, cyanoalkyl, cycloalkyl, cycloalkylalkyl, ethylenedioxy, formyl, formylalkyl, haloalkoxy, haloalkyl, haloalkylthio, halogen, hydroxy, hydroxyalkyl, mercapto, mercaptoalkyl, nitro, —$NZ_CZ_D$, ($NZ_CZ_D$)alkyl, ($NZ_CZ_D$)carbonyl, ($NZ_CZ_D$)carbonylalkyl, ($NZ_CZ_D$)sulfonyl, —$NR_AS(O)_2R_B$, —$S(O)_2OR_A$ and —$S(O)_2 R_A$ wherein $R_A$ and $R_B$ are as defined herein. Representative examples include, but are not limited to, 2,6-dimethylmorpholinyl, 4-(3-chlorophenyl)-1-piperazinyl, 4-(3,4-dimethylphenyl)-1-piperazinyl, 4-(4-chlorophenyl)-1-piperazinyl, 4-(4-methylphenyl)-3-methyl-1-piperazinyl, 4-(2,3-dimethylphenyl)-1-piperazinyl, 4-(2,3-dichlorophenyl)-1-piperazinyl, 4-(3,4-dichlorophenyl)-1-piperazinyl, 4-[3-(trifluoromethyl)phenyl]-1-piperazinyl, 4-(4-bromophenyl)-1-piperazinyl, 4-[4-(trifluoromethyl)-2-pyridinyl]-1-piperazinyl, 2-oxo-1-pyrrolidinyl, 5-(trifluoromethyl)-2-pyridinyl, 6-(trifluoromethyl)-3-pyridinyl.

The term "heterocyclealkyl" as used herein, means a heterocycle, as defined herein, appended to the parent molecular moiety through an alkyl group, as defined herein. Representative examples of heterocyclealkyl include, but are not limited to, pyridin-3-ylmethyl and 2-pyrimidin-2-ylpropyl.

The term "heterocycleoxy" as used herein, means a heterocycle group, as defined herein, appended to the parent molecular moiety through an oxygen atom. Representative examples of heterocycleoxy include, but are not limited to, pyridin-3-yloxy and quinolin-3-yloxy.

The term "heterocyclethio" as used herein, means a heterocycle group, as defined herein, appended to the parent molecular moiety through a sulfur atom. Representative examples of heterocyclethio include, but are not limited to, pyridin-3-ylsulfanyl and quinolin-3-ylsulfanyl.

The term "hydroxy" as used herein, means an —OH group.

The term "hydroxyalkyl" as used herein, means at least one hydroxy group, as defined herein, appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto" as used herein, means a —SH group.

The term "mercaptoalkyl" as used herein, means a mercapto group, as defined herein, appended to the parent molecular moiety through an alkyl group, as defined herein. Representative examples of mercaptoalkyl include, but are not limited to, 2-mercaptoethyl and 3-mercaptopropyl.

The term "methylenedioxy" as used herein, means a —$OCH_2O$— group wherein the oxygen atoms of the methylenedioxy are attached to the parent molecular moiety through two adjacent carbon atoms.

The term "nitro" as used herein, means a —$NO_2$ group.

The term "—$NZ_AZ_B$" as used herein, means two groups, $Z_A$ and $Z_B$, which are appended to the parent molecular moiety through a nitrogen atom. $Z_A$ and $Z_B$ are each independently selected from the group consisting of: hydrogen, alkyl, alkylcarbonyl, formyl, aryl and arylalkyl. Representative examples of —$NZ_AZ_B$ include, but are not limited to, amino, methylamino, acetylamino, benzylamino, phenylamino, and acetylmethylamino.

The term "($NZ_AZ_B$)alkyl" as used herein, means a —$NZ_AZ_B$ group, as defined herein, appended to the parent molecular moiety through an alkyl group, as defined herein. Representative examples of ($NZ_AZ_B$)alkyl include, but are not limited to, aminomethyl, 2-(methylamino)ethyl, 2-(dimethylamino)ethyl and (ethylmethylamino)methyl.

The term "($NZ_AZ_B$)alkylcarbonyl" as used herein, means a ($NZ_AZ_B$)alkyl group, as defined herein, appended to the parent molecular moiety through a carbonyl group, as defined herein. Representative examples of ($NZ_AZ_B$)alkylcarbonyl include, but are not limited to, dimethylaminomethylcarbonyl, 2-(dimethylamino)ethylcarbonyl, and (ethylmethylamino)methylcarbonyl.

The term "($NZ_AZ_B$)carbonyl" as used herein, means a —$NZ_AZ_B$ group, as defined herein, appended to the parent molecular moiety through a carbonyl group, as defined herein. Representative examples of ($NZ_AZ_B$)carbonyl include, but are not limited to, aminocarbonyl, (methylamino)carbonyl, (dimethylamino)carbonyl and (ethylmethylamino)carbonyl.

The term "($NZ_AZ_B$)carbonylalkyl" as used herein, means a ($NZ_AZ_B$)carbonyl group, as defined herein, appended to the parent molecular moiety through an alkyl group, as defined herein. Representative examples of ($NZ_AZ_B$)carbonylalkyl include, but are not limited to, (aminocarbonyl)methyl, 2-((methylamino)carbonyl)ethyl and ((dimethylamino)carbonyl)methyl.

The term "($NZ_AZ_B$)sulfonyl" as used herein, means a —$NZ_AZ_B$ group, as defined herein, appended to the parent molecular moiety through a sulfonyl group, as defined herein. Representative examples of ($NZ_AZ_B$)sulfonyl include, but are not limited to, aminosulfonyl, (methylamino)sulfonyl, (dimethylamino)sulfonyl and (ethylmethylamino)sulfonyl.

The term "—$NZ_AZ_B$" as used herein, means two groups, $Z_A$ and $Z_B$, which are appended to the parent molecular moiety through a nitrogen atom. $Z_A$ and $Z_B$ are each independently selected from the group consisting of: hydrogen, alkyl, alkylcarbonyl, formyl, aryl and arylalkyl. Representative examples of —$NZ_AZ_B$ include, but are not limited to, amino, methylamino, acetylamino, benzylamino, phenylamino, and acetylmethylamino.

The term "—$NZ_CZ_D$" as used herein, means two groups, $Z_C$ and $Z_D$, which are appended to the parent molecular moiety through a nitrogen atom. $Z_C$ and $Z_D$ are each independently selected from the group consisting of: hydrogen, alkyl, alkylcarbonyl, formyl, aryl and arylalkyl. Representative examples of —$NZ_CZ_D$ include, but are not limited to, amino, methylamino, acetylamino, benzylamino, phenylamino, and acetylmethylamino.

The term "($NZ_CZ_D$)alkyl" as used herein, means a —$NZ_CZ_D$ group, as defined herein, appended to the parent molecular moiety through an alkyl group, as defined herein. Representative examples of $(NZ_CZ_D)$alkyl include, but are not limited to, aminomethyl, 2-(methylamino)ethyl, 2-(dimethylamino)ethyl and (ethylmethylamino)methyl.

The term "$(NZ_CZ_D)$carbonyl" as used herein, means a —$NZ_CZ_D$ group, as defined herein, appended to the parent molecular moiety through a carbonyl group, as defined herein. Representative examples of $(NZ_CZ_D)$carbonyl include, but are not limited to, aminocarbonyl, (methylamino)carbonyl, (dimethylamino)carbonyl and (ethylmethylamino)carbonyl.

The term "$(NZ_CZ_D)$carbonylalkyl" as used herein, means a $(NZ_CZ_D)$carbonyl group, as defined herein, appended to the parent molecular moiety through an alkyl group, as defined herein. Representative examples of $(NZ_CZ_D)$carbonylalkyl include, but are not limited to, (aminocarbonyl)methyl, 2-((methylamino)carbonyl)ethyl and ((dimethylamino)carbonyl)methyl.

The term "$(NZ_CZ_D)$sulfonyl" as used herein, means a —$NZ_CZ_D$ group, as defined herein, appended to the parent molecular moiety through a sulfonyl group, as defined herein. Representative examples of $(NZ_CZ_D)$sulfonyl include, but are not limited to, aminosulfonyl, (methylamino)sulfonyl, (dimethylamino)sulfonyl and (ethylmethylamino)sulfonyl.

All hydrocarbons can be substituted with a heteroatom, such as O, S and N.

The term "oxo" as used herein, means =O.

The term "sulfonyl" as used herein, means a —$S(O)_2$— group.

The compounds of the present invention can be used in the form of pharmaceutically acceptable salts derived from inorganic or organic acids. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio.

Pharmaceutically acceptable salts are well-known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid. Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The term "pharmaceutically acceptable prodrug" or "prodrug," as used herein, represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use.

Compounds of the present invention were named by ACD/ChemSketch version 5.0 (developed by Advanced Chemistry Development, Inc., Toronto, ON, Canada) or were given names which appeared to be consistent with ACD nomenclature.

Abbreviations

Abbreviations which have been used in the descriptions of the Schemes and the Examples that follow are: dba for dibenzylideneacetone; DBU for 1,8-diazabicyclo[5.4.0]undec-7-ene; BINAP for 2,2'-bis(diphenylphosphino)-1,1'-binaphthyl; DCC for 1,3-dicyclohexylcarbodiimide; DIEA for diisopropylethylamine; DMAP for 4-dimethylaminopyridine; DMF for N,N-dimethylformamide; DMSO for dimethylsulfoxide; EDCI or EDC for 1-ethyl-3-[3-(dimethylamino)propyl]-carbodiimide hydrochloride; HMPA for hexamethylphosphoramide; HPLC high pressure liquid chromatography; NBS for N-bromosuccinimide; Pd for palladium; Ph for phenyl; psi for pounds per square inch; and THF for tetrahydrofuran.

Preparation of Compounds of the Present Invention

The compounds and processes of the present invention will be better understood in connection with the following Examples. The following Examples are intended as an illustration of, and not a limitation upon, the scope of the invention as defined in the appended claims.

Examples 1-3 refer to in part Scheme 5, reproduced below.

Scheme 5

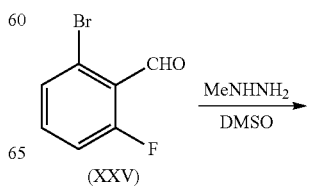

(XXV)

-continued

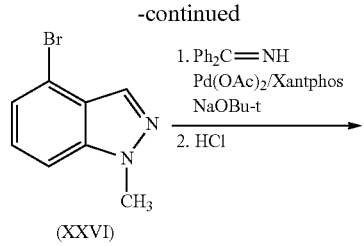

(XXVI)

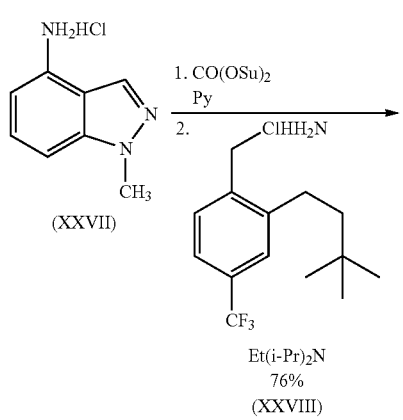

(XXVIII)

Example 1

4-Bromo-1-methylindazole (XXVI)

A solution of crude 2-bromo-6-fluorobenzaldehyde (42 g, 0.2 mol) (XXV) in DMSO (44 mL) was added to methylhydrazine (63 g, 7 eq) while maintaining the internal temperature to less than 35° C. The mixture was then heated to 80° C. for 22 hours, after which the internal temperature was adjusted to 25° C. The mixture was diluted with water (160 mL) and heptanes (160 mL) while maintaining the internal temperature at less than 40° C. The layers were separated, and the aqueous layer was extracted with heptanes (40 mL). Combined organic layers were washed with 10% citric acid (100 mL) and concentrated in vacuo. The product solidified on standing to give a yellowish solid (27.5 g, 70% yield)

$^1$H NMR (CDCl3, 400 mHz): 8.04 (1H, s); 7.29-7.27 (2H, m); 7.12-7.10 (1H, m); 4.07 (3H, s).

Example 2

1-Methyl-4-aminoindazole Hydrochloride

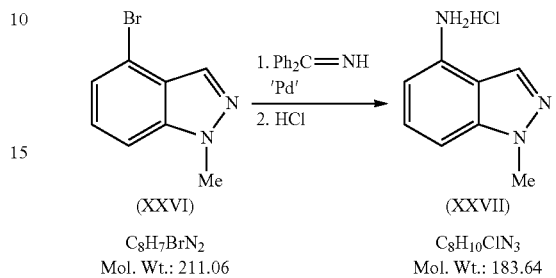

(XXVI)
$C_8H_7BrN_2$
Mol. Wt.: 211.06

(XXVII)
$C_8H_{10}ClN_3$
Mol. Wt.: 183.64

Palladium acetate (82 mg, 2% mol) and Xantphos (9,9-Dimethyl-4,5-bis(diphenylphosphino)xanthene; 287 mg, 3% mol) were dissolved in toluene (10 mL) and mixed at room temperature for 5 min. To the resulting solution was added a solution of 4-bromo-1-methylindazole (3.68 g, 17.4 mmol) and benzophenone imine (3.0 g, 17.4 mmol) in toluene (30 mL). The resulting solution was evacuated and purged with nitrogen two times, then mixed at room temperature for at least 15 min. NaOBu-t (1.9 g, 1.4 eq) was then added, and the mixture was evacuated and purged with nitrogen again.

The mixture was heated to 80-85° C. for 2 hours (complete by HPLC). Then the mixture was cooled to room temperature and diluted with water (30 mL). The aqueous layer was separated and extracted with toluene (~20 mL). 6 N HCl (10 mL) was added to the combined organic layer. After 1 hour at room temperature (hydrolysis complete by HPLC), water (40 mL) was added to dissolve the solids. Toluene layer was discarded, and the aqueous layer filtered to remove some insoluble material. The pH of aqueous layer was adjusted to 14 with 50% NaOH and the product precipitated. The product was filtered and dissolved in acetonitrile (25 mL). Concentrated hydrochloric acid was added drop-wise to attain a pH 1. The precipitate was filtered, washed with water and dried to 2.55 g (80%) of white solid.

$^1$H NMR (DMSO-$d_6$, 400 mHz): 10.6 (3H, br.s); 8.25 (1H, s); 7.59 (1H, d); 7.40 (1H, dd); 7.13 (1H, d); 4.06 (3H, s)

Example 3

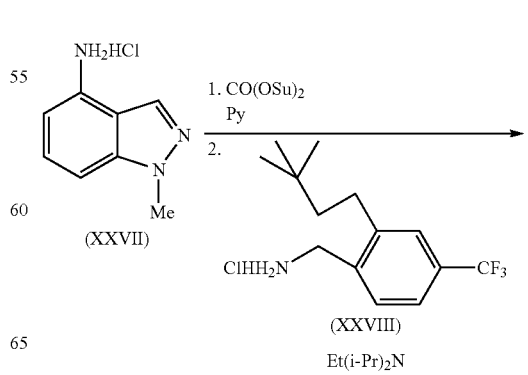

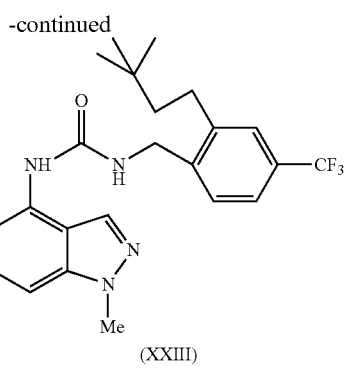

Pyridine (8.0 g, 101 mmol, 2.07 eq) was added over approximately 5 minutes to a slurry of 1-methyl-4-aminoindazole hydrochloride (9.0 g, 49 mmol) and disuccinimidyl-carbonate (13.2 g, 51.5 mmol, 1.05 eq) in acetonitrile (125 mL) while maintaining the internal temperature at less than 25° C. After 15 minutes, water (about 10 drops) was added. After 10 minutes, benzylamine hydrochloride (14.9 g, 1 eq) was added in one portion, followed by diisopropylethylamine (19.25 g, 0.15 m, 3 eq) over ~10 minutes while maintaining the internal temperature at less then 25° C. After 30 minutes (complete reaction by HPLC), water (100 mL) was added slowly to precipitate the product, which was filtered, washed with 100 mL (1:1 ACN-water) and dried at 50° C. in vacuum. Product (18.7 g (85% yield)) was obtained that had a pinkish color. The color was removed by recrystallization from ethyl acetate/heptanes.

Crude product was dissolved in ethyl acetate (46 ml) at 70° C., then precipitated by slow addition of heptanes (184 mL) at 65° C.-70° C. The mixture was cooled to room temperature, filtered, washed with 40 ml of 4:1 heptanes:ethyl acetate, and dried in vacuo.

The following Examples refer in part to Scheme 4, reproduced below.

Scheme 4

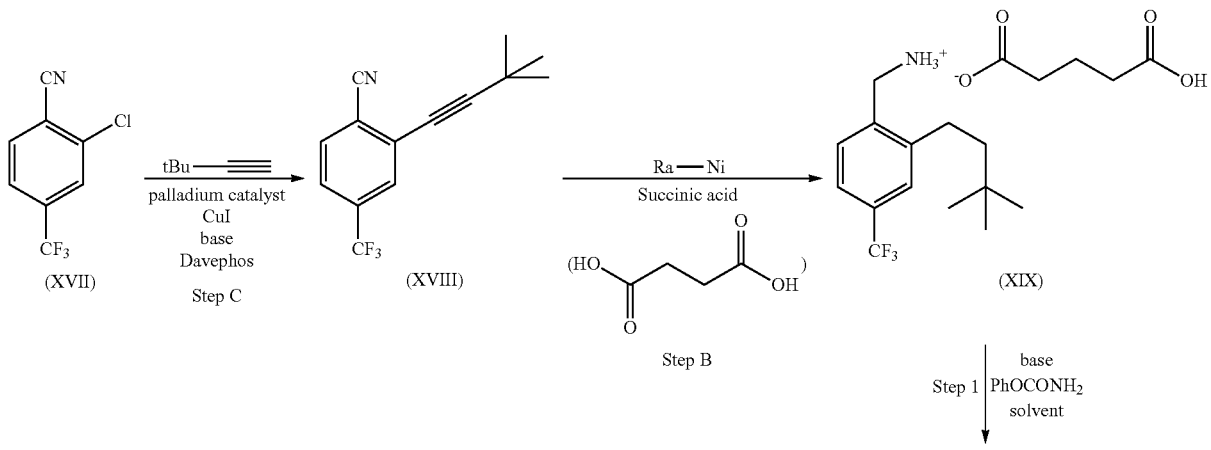

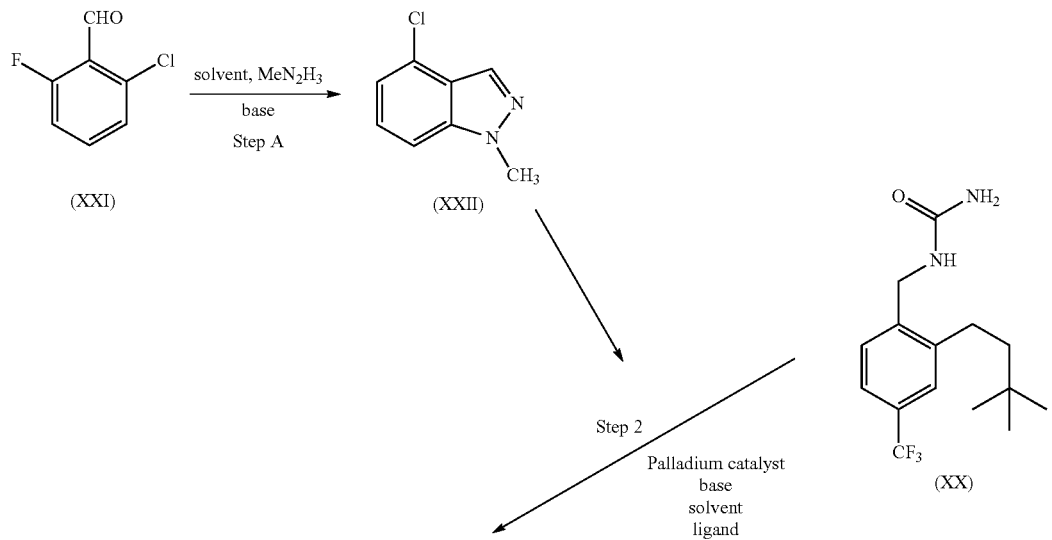

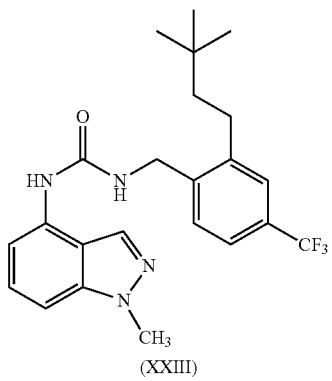

(XXIII)

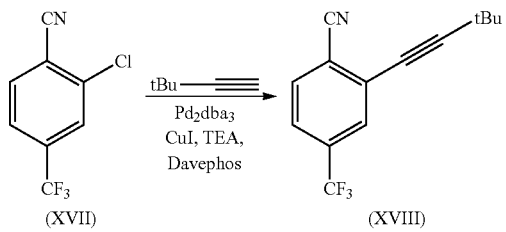

To a flask was added Pd$_2$dba$_3$ (0.405 g), DavePhos (0.6884 g, 1.75 mmol), and CuI (0.1655 g). This was purged with nitrogen and degassed; triethylamine (100 mL) was then added. Benzonitrile (XVII) (36.2 g, 176 mmol) was then added, and the mixture was heated to 65° C. 3,3-dimethylbutyne (23.7 g, 288 mmol) was then slowly added over 2 hours. The mixture was heated an additional 2 hours, and the heat removed. The mixture was diluted with isopropyl acetate (150 mL) and washed twice with water (150 mL) and twice with 10% aqueous citric acid (150 mL). The organics were diluted with methanol (40 mL), and the volume reduced in vacuo to 60 mL. This was repeated twice with 190 mL methanol, the residual material diluted to 250 g with methanol and used in the next step as a solution. An analytical sample was obtained by removing all the solvent in vacuo.

$^1$H NMR (CDCl$_3$, 400 mHz) 7.75-7.70 (m, 2H), 7.60-7.55 (m, 1H), 1.37 (s, 9H); $^{13}$C NMR (CDCl$_3$, 100 MHz) 132.6, 128.7, 128.6, 123.8, 123.7, 116.24, 107.96, 75.06, 30.73, 28.64.

Example 5

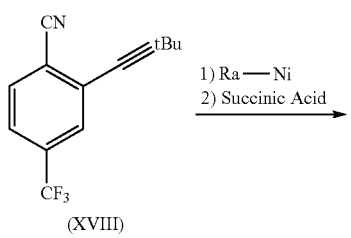

Example 4

-continued

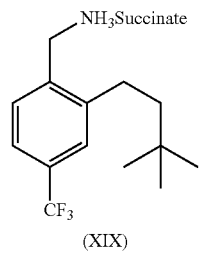

(XIX)

To a flask containing Raney Nickel (19 g) was added alkyne (XVIII) in methanol (134 g, 14.9 wt % (XVIII)), potassium hydroxide (0.2305 g), and additional methanol (44.3 g). The mixture was pressurized with hydrogen and agitated for 42 hours. The solution was filtered, and the cake washed with methanol (20 g). To the solution was added succinic acid (10.65 g, 1.2 equiv). The solution was reduced in vacuo to 100 mL, diluted with isopropanol (100 mL), and concentrated again to 100 mL. The slurry was filtered and the wet cake washed with isopropanol (120 mL). The cake was dried under vacuum at 35° C. to give a white solid.

$^1$H NMR (CD$_3$OD, 400 mHz) 7.60-7.55 (3H, m); 4.21 (2H, s); 2.78-2.74 (2H, m); 2.51 (4H, s); 1.49-1.45 (2H, m); 1.04 (9H, s); $^{13}$C NMR (CD$_3$OD, 100 MHz) 178.4, 144.0, 136.9, 132.0, 131.7, 130.0, 127.0, 123.9, 46.8, 40.6, 32.7, 31.6, 29.7, 29.1.

Example 6

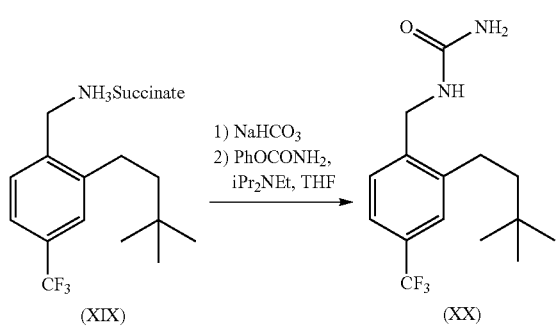

To 14.0 g of succinate salt (XIX) was added toluene (150 mL), followed by 70 mL of 5% NaOH. The separated organic layer was washed twice with 5% NaHCO$_3$ (50 mL) followed by 20% brine (50 mL), and then concentrated and chased with 2-methyl THF to give benzylamine free base. The yield of free base is typically 99.8%. To a slurry of phenyl carbamate (5.12 g, 1.07 eq) in 2-methyl THF (25 mL) was added N,N-di-isopropyl ethylamine (8.77 g, 2 equiv) and benzylamine/2-methyl THF solution (total solvent approximately 50 mL). The mixture was stirred at 45° C. overnight and cooled to 20° C. Isopropyl acetate (55 mL) was added, and the organics then washed twice with 5% NaOH (50 mL each), followed three times by 20% NaCl (50 mL each). The organic layer was concentrated and chased with methanol to approximately 30 mL. To the residue was added 40 mL methanol. The resulting mixture was heated to 50-60° C., and water (80 mL) was slowly added. The slurry was cooled to 20° C., filtered and washed with 50% aqueous methanol followed by water. The wet cake was dried at 55° C. to give 18.8 g of urea (XX) in 98% yield.

$^1$H NMR (d$_6$-DMSO, 400 mHz) 7.50 (1H, d, J=8.0 Hz); 7.45 (1H, s); 7.40 (1H, d, J=8.1 Hz); 6.42 (1H, t, J=5.7 Hz); 5.57 (2H, s); 4.25 (2H, d, J=5.9 Hz); 2.65-2.60 (2H, m); 1.41-1.37 (2H, m); 0.96 (9H, s); $^{13}$C NMR (d$_6$-DMSO, 100 MHz) 157.9, 142.4, 141.2, 127.5, 124.8, 121.9, 44.7, 39.9, 30.5, 29.1, 27.1.

(85769-162)

Example 7

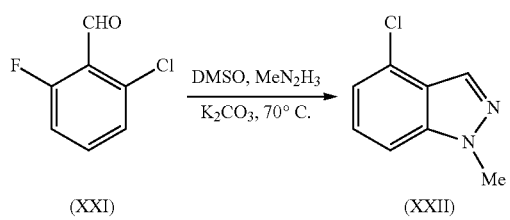

To a flask was added potassium carbonate (55.0 g, 0.4 mol, 2 equiv), formula XXI (32.1 g, 0.2 mol), and DMSO (317 g). At ambient temperature, methyl hydrazine (47.3 g, 1.03 mol, 5 equiv) was added. The mixture was then heated at 70° C. for 7 days. The mixture was cooled to ambient and diluted with water (250 mL) and methyl t-butyl ether (950 mL). The upper organics were separated, and the lower layer was re-extracted with methyl-t-butyl ether (910 mL). The combined organics were washed with 10% citric acid (125 mL), water (1250 mL) and concentrated to oil. To the oil was added water (125 mL). The resulting solid was filtered, washed with water and dried at 30° C. to yield 27.4 g of crude compound XXII. Purification of compound XXII: To a 0 to 5° C. solution of crude XXII (173 g) in methanol (260 mL), water (250 mL) was slowly added. The resulting solid was filtered and washed with 33% methanol/67% water (150 mL total) followed by water. 155 g of solid were recovered after drying at 30° C.

$^1$H NMR (CDCl$_3$, 400 mHz) 8.03 (1H, s); 7.29-7.25 (1H, m); 7.26 (1H, s); 7.13-7.09 (1H, m); 4.06 (3H, s); $^{13}$C NMR (CDCl$_3$, 100 MHz) 140.4, 131.1, 126.5, 126.3, 122.9, 119.8, 107.3, 36.1.

Example 8

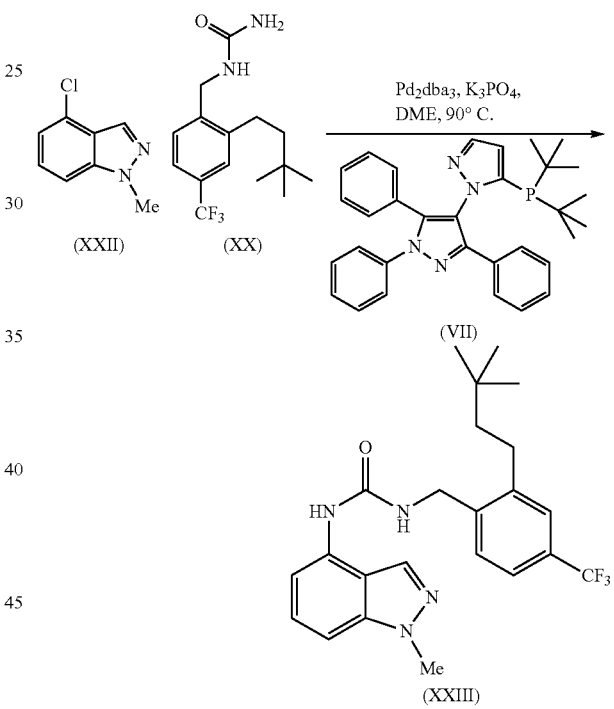

To a flask was added urea of formula (XX) (20 g, 66.15 mmol), indazole of formula (XXII) (13.23 g, 79.38 mmol), potassium carbonate (21.04 g, 99.23 mmol), Pd$_2$dba$_3$ (606 mg, 0.66 mmol), and (VII) (1.34 g, 2.65 mmol). After purging with nitrogen, the mixture was diluted with purged dimethoxyethane (DME, 300 mL). The mixture was heated to 80° C. for 18 hours, and additional Pd$_2$dba$_3$ (150 mg, 0.33 mmol) and ligand (VII) (337 mg, 6.0 mmol) were added. After an additional 1.5 hours of heating, the mixture was cooled to ambient, filtered, and concentrated to approximately 150 g. The residue was chased and distilled twice with isopropanol (2×500 mL). The remaining material was diluted to approximately 230 g with isopropanol and heated to 65° C. Water (182 g) was slowly added, and the solution cooled to 0° C. The slurry was stirred at 0° C. for 1 hour, filtered, and the cake washed with 45% water/methanol (100 mL). The solids were dried at 40° C. to give 24.0 g of product (XXIII).

$^1$H NMR (d$_6$-DMSO, 400 mHz) 8.83 (1H, s); 8.03 (1H, d, J=0.7 Hz); 7.62 (1H, d, J=7.4 Hz); 7.55-7.49 (3H, m); 7.23 (1H, dd, J=7.95, 7.95 Hz); 7.13 (1H, d, J=8.4 Hz); 6.81 (1H, dd, J=5.7, 5.7 Hz); 4.44 (2H, d, J=5.6 Hz); 3.98 (3H, s); 2.71-2.66 (2H, m); 1.46-1.41 (2H, m); 0.96 (9H, s); $^{13}$C NMR (d$_6$-DMSO, 100 MHz) 154.2, 141.5, 140.0, 132.4, 129.2, 127.9, 127.3, 126.6, 125.0, 122.1, 115.9, 114.9, 106.7, 102.2, 44.9, 40.0, 35.4, 30.5, 29.1, 27.2.

(87909-45)

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

We claim:

1. A method of making a compound of formula XXIV,

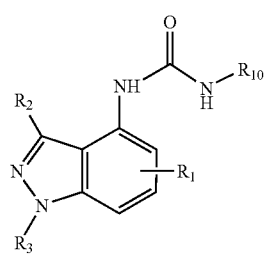

(XXIV)

or salt thereof, comprising:
reacting a compound of formula XII or XIIa,

R$_{10}$—CN    (XII)

or

R$_{10}$—NH$_2$    (XIIa)

with hydrogen in the presence of Ra—Ni, and then an acid HX, to produce a compound of formula XIII or XIIIa,

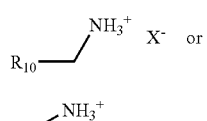

(XIII)

(XIIIa)

reacting the freebase of compound of formula XIII or XIIIa with PhOCONH$_2$ in the presence of a first base and a first solvent, to produce a compound of formula IV,

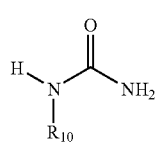

(IV)

optionally, reacting a compound of formula XII or XIIa,

R$_{10}$—CN    (XII)

or

R$_{10}$—NH$_2$    (XIIa)

with PhOCONH$_2$ in the presence of a first base and a first solvent, to produce a compound of formula IV,

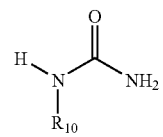

(IV)

or further optionally reacting a compound of formula XII or XIIa, in situ,

R$_{10}$—CN    (XII)

or

R$_{10}$—NH$_2$    (XIIa)

with hydrogen in the presence of Ra—Ni, and an acid HX, and PhOCONH$_2$ in the presence of a first base and a first solvent, to produce a compound of formula IV,

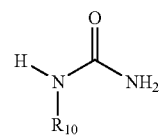

(IV)

and further reacting the compound of formula IV with a compound of formula II

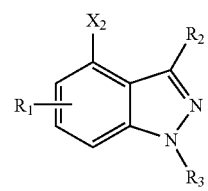

(II)

in the presence of a palladium catalyst, a second base, a second solvent, and a ligand,
wherein X$_2$ is selected from the group consisting of: halogen and sulfonate, wherein the sulfonate is independently substituted with fluorine or C$_1$-C$_8$ fluorinated alkanes;
wherein the compound of formula II includes at least one R$_1$ group;
wherein R$_1$ may be present more than once on the indicated ring;
wherein each wherein each R$_1$ is independently selected from the group consisting of: hydrogen, hydroxyl, alkoxy, amino, substituted amino, substituted sulfur, halogen, aryl, substituted aryl, heteroaryl, substituted heteroaryl, heterocyclic, substituted heterocyclic, C$_1$-C$_8$ alkyl, C$_2$-C$_8$ alkenyl, C$_2$-C$_8$ alkynyl, substituted C$_1$-C$_8$ alkyl, substituted C$_2$-C$_8$ alkenyl, substituted —C$_2$-C$_8$ alkynyl; —C₃-C₁₂ cycloalkyl, substituted —C₃-C₁₂ cycloalkyl, —C₃-C₁₂ cycloalkenyl, and substituted —C₃-C₁₂ cycloalkenyl; each containing 0, 1, 2, or 3 heteroatoms selected from the group consisting of: O, S, and N;

R₂ is selected from the group consisting of: hydrogen, alkyl, and aryl;

R₃ is selected from the group consisting of: hydrogen, aryl, substituted aryl, heteroaryl, substituted heteroaryl, heterocyclic, substituted heterocyclic, —C₁-C₈ alkyl, —C₂-C₈ alkenyl, —C₂-C₈ alkynyl, substituted —C₁-C₈ alkyl, substituted —C₂-C₈ alkenyl, substituted —C₂-C₈ alkynyl; —C₃-C₁₂ cycloalkyl, substituted —C₃-C₁₂ cycloalkyl, —C₃-C₁₂ cycloalkenyl, and substituted —C₃-C₁₂ cycloalkenyl; each containing 0, 1, 2, or 3 heteroatoms selected from the group consisting of: O, S, and N; and R₁₀ is selected from the group consisting of: aryl, substituted aryl, heteroaryl, substituted heteroaryl, heterocyclic, substituted heterocyclic, —C₁-C₈ alkyl, —C₂-C₈ alkenyl, —C₂-C₈ alkynyl, substituted —C₁-C₈ alkyl, substituted —C₂-C₈ alkenyl, substituted —C₂-C₈ alkynyl; —C₃-C₁₂ cycloalkyl, substituted —C₃-C₁₂ cycloalkyl, —C₃-C₁₂ cycloalkenyl, and substituted —C₃-C₁₂ cycloalkenyl; each containing 0, 1, 2, or 3 heteroatoms selected from the group consisting of: O, S, and N.

2. The method of claim 1, wherein X₂ is Cl, R₃ is hydrogen or methyl, and R₁₀ is aryl or alkyl.

3. The method of claim 1, wherein R₁₀ is a group of formula VIII or VIIIa

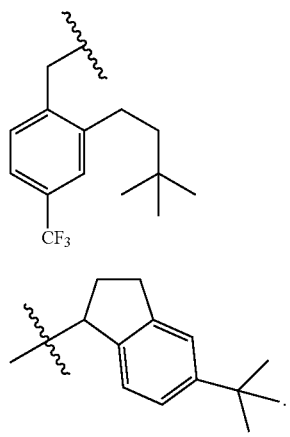

4. The method of claim 1, wherein the first base is N,N-diisopropyl ethyl amine, and the second base is potassium phosphate tribasic.

5. The method of claim 1, wherein the first solvent is Me-THF, and the second solvent is DME.

6. The method of claim 1, wherein the palladium catalyst is selected from the group consisting of: Pd₂(dba)₃, Pd₂Cl₂(dba), Pd(OAc)₂, Pd(OTFA)₂, PdCl₂, PdCl₂(CH₃CN)₂, and PdCl₂(PhCN)₂.

7. The method of claim 6, wherein the palladium catalyst is Pd₂dba₃.

8. The method of claim 1, wherein the ligand is selected from the group consisting of the compounds of formulas XXX, XXXI, XXXII, XXXIII, XXXIV, XXXV, XXXVI, XXXVII, XXXVIII, XXXIX, and VII:

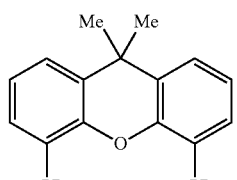
(XXX) R = Ph
(XXXI) R = 3,5-(CF₃)₂Ph

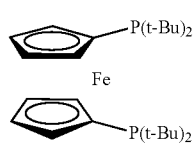
(XXXII)

(XXXIII)

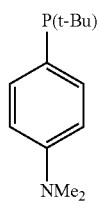
(XXXIV)

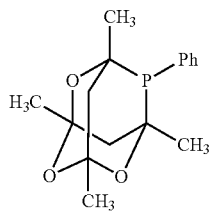
(XXXV)

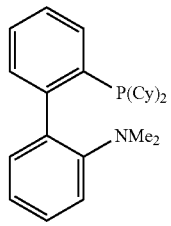
(XXXVI)

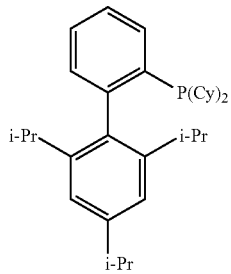
(XXXVII)

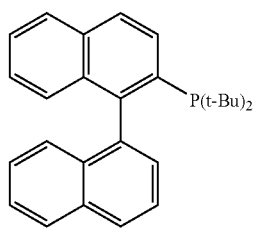

-continued
(XXXVIII) 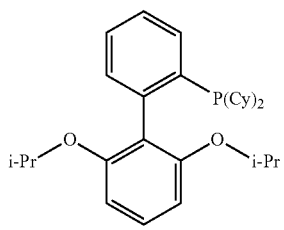
(XXXIX) 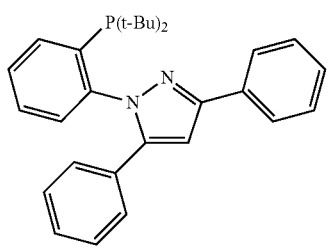
(VII) 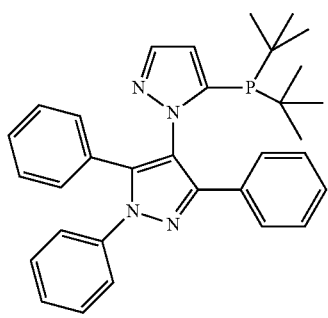
PdCl$_2$(dppf), and PdCl$_2$(dppf)CH$_2$Cl$_2$.
9. The method of claim 8, wherein the ligand is a compound of formula VII
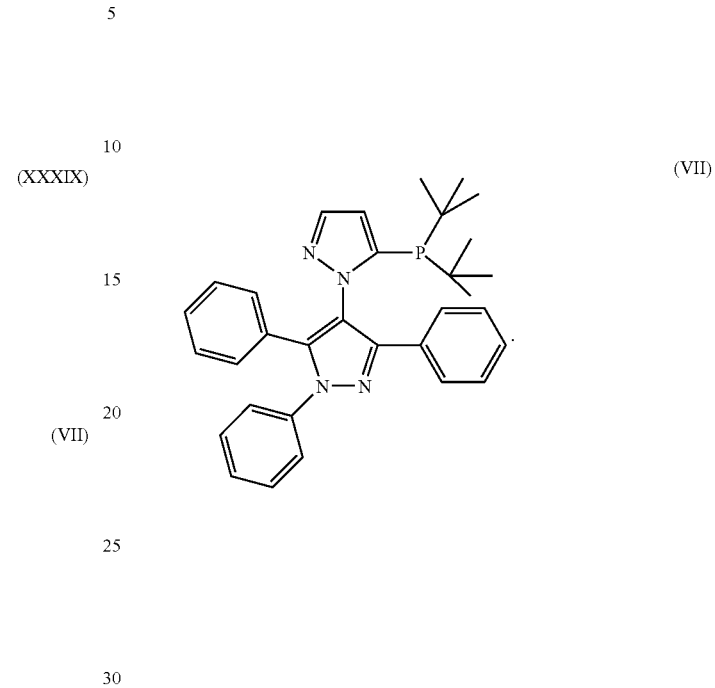
* * * * *